(12) United States Patent
Tsushima

(10) Patent No.: US 10,845,473 B2
(45) Date of Patent: Nov. 24, 2020

(54) ULTRASOUND SIGNAL PROCESSING DEVICE, ULTRASOUND SIGNAL PROCESSING METHOD, AND ULTRASOUND DIAGNOSTIC DEVICE

(71) Applicant: Konica Minolta, Inc., Tokyo (JP)

(72) Inventor: Mineo Tsushima, Kyoto-fu (JP)

(73) Assignee: KONICA MINOLTA, INC., Tokyo (JP)

( * ) Notice: Subject to any disclaimer, the term of this patent is extended or adjusted under 35 U.S.C. 154(b) by 539 days.

(21) Appl. No.: 15/630,400

(22) Filed: Jun. 22, 2017

(65) Prior Publication Data
US 2018/0011178 A1 Jan. 11, 2018

(30) Foreign Application Priority Data
Jul. 5, 2016 (JP) ................................. 2016-133382

(51) Int. Cl.
*G01S 7/00* (2006.01)
*G01S 7/52* (2006.01)
(Continued)

(52) U.S. Cl.
CPC ............ *G01S 7/52087* (2013.01); *A61B 8/14* (2013.01); *A61B 8/4477* (2013.01);
(Continued)

(58) Field of Classification Search
CPC ............ G01S 7/52087; G01S 7/52026; G01S 15/8915; G01S 15/8997; A61B 8/14; A61B 8/4477; A61B 8/5207; G10K 11/346
See application file for complete search history.

(56) References Cited

U.S. PATENT DOCUMENTS 4,214,269 A * 7/1980 Parker ..................... G01S 7/298
342/185
4,245,250 A * 1/1981 Tiemann .............. G01S 7/52044
342/185
(Continued)

FOREIGN PATENT DOCUMENTS

CN 104703544 A 6/2015
JP 2016-087453 A 5/2016

OTHER PUBLICATIONS

Extended European Search Report dated Nov. 23, 2107 from corresponding European Patent Application No. 17177101.7.
(Continued)

*Primary Examiner* — Joanne M Hoffman
(74) *Attorney, Agent, or Firm* — Lucas & Mercanti, LLP

(57) ABSTRACT

Ultrasound signal processing device including: transmitter performing transmission events while varying a focal point; receiver generating, for each transmission event, receive signal sequences for transducer elements; delay-and-sum calculator generating, for each transmission event, a sub-frame acoustic line signal including an acoustic line signal for each measurement point located on target lines passing through the focal point and composing a target line group; and synthesizer combining sub-frame acoustic line signals to generate a frame acoustic line signal. The target lines are straight lines, and any measurement point, on any target line, that is spaced away from the focal point by a predetermined distance or more satisfies a condition that distance between the measurement point and a most nearby measurement point on the same target line is smaller than distance between the measurement point and a most nearby one among measurement points on an adjacent target line.

11 Claims, 20 Drawing Sheets

(51) Int. Cl.
    *G01S 15/89*    (2006.01)
    *G10K 11/34*    (2006.01)
    *A61B 8/14*     (2006.01)
    *A61B 8/00*     (2006.01)
    *A61B 8/08*     (2006.01)

(52) U.S. Cl.
    CPC ........ *A61B 8/5207* (2013.01); *G01S 7/52026* (2013.01); *G01S 15/8915* (2013.01); *G01S 15/8997* (2013.01); *G10K 11/346* (2013.01)

(56) References Cited

U.S. PATENT DOCUMENTS

| | | | | |
|---|---|---|---|---|
| 4,827,268 | A * | 5/1989 | Rosen | H01Q 3/40 342/368 |
| 6,918,876 | B1 * | 7/2005 | Kamiyama | G01S 7/52071 600/437 |
| 9,482,736 | B1 * | 11/2016 | Ray | G01S 3/808 |
| 2002/0049381 | A1 * | 4/2002 | Eck | G01S 15/8915 600/447 |
| 2004/0039285 | A1 * | 2/2004 | Ustuner | G01S 7/52071 600/459 |
| 2005/0033165 | A1 * | 2/2005 | Ustuner | G01S 7/52047 600/437 |
| 2009/0069693 | A1 * | 3/2009 | Burcher | G01S 15/8995 600/459 |
| 2010/0030076 | A1 * | 2/2010 | Vortman | A61N 7/02 600/439 |
| 2013/0308850 | A1 * | 11/2013 | Oikawa | G01S 15/8945 382/131 |
| 2013/0338506 | A1 * | 12/2013 | Kim | G01S 7/52095 600/447 |
| 2014/0078866 | A1 * | 3/2014 | Kanamori | A61B 8/4461 367/87 |
| 2014/0187925 | A1 * | 7/2014 | Corl | A61B 8/0891 600/425 |
| 2014/0364738 | A1 * | 12/2014 | Huang | A61B 8/5207 600/447 |
| 2015/0196273 | A1 * | 7/2015 | Yamamoto | G01S 7/52047 600/447 |
| 2016/0120503 | A1 * | 5/2016 | Tsushima | A61B 8/5207 367/7 |
| 2016/0243381 | A1 * | 8/2016 | Alford | A61N 7/00 |
| 2018/0003811 | A1 * | 1/2018 | Pellegretti | A61B 8/4461 |
| 2018/0214123 | A1 * | 8/2018 | Takano | A61B 8/4405 |
| 2018/0303461 | A1 * | 10/2018 | Tsushima | A61B 8/54 |

OTHER PUBLICATIONS

S.I. Nikolov, et al; Virtual ultrasound sources in high-resolution ultrasound imaging; Proc. SPIE; vol. 4687; 2002; pp. 395-405.
M. Itou, et al; Ultrasound diagnostic equipment; Corona Publishing Co., Ltd; Aug. 2002; pp. 42-45 (partial translation).
CNIPA, Office Action for the corresponding Chinese Patent Application No. 201710518717.9, dated Nov. 4, 2019, with English translation (23 pages).
JPA, Office Action for the corresponding Japanese Patent Application No. 2016-133382, dated Jan. 14, 2020, with English translation.
Office Action for the corresponding Chinese Patent Application No. 201710518717.9, dated Jul. 1, 2020, with English translation (27 pages).

* cited by examiner

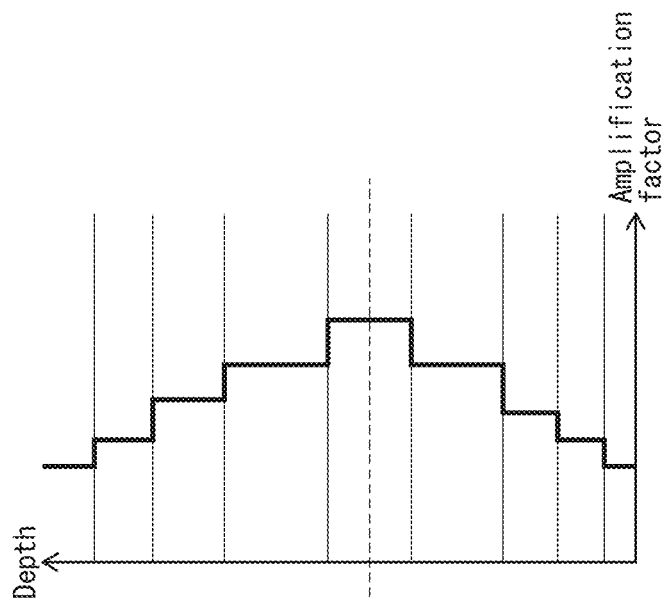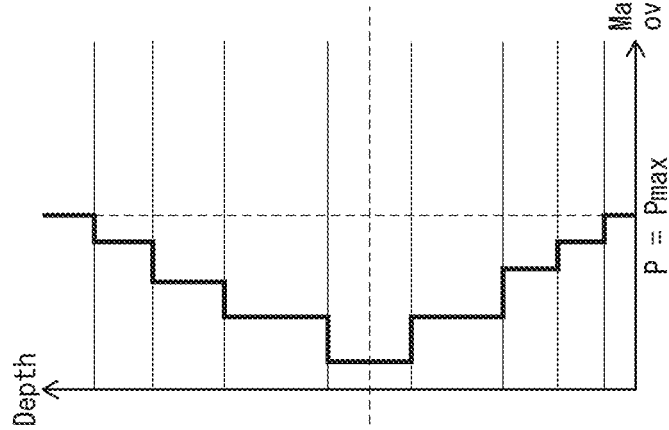

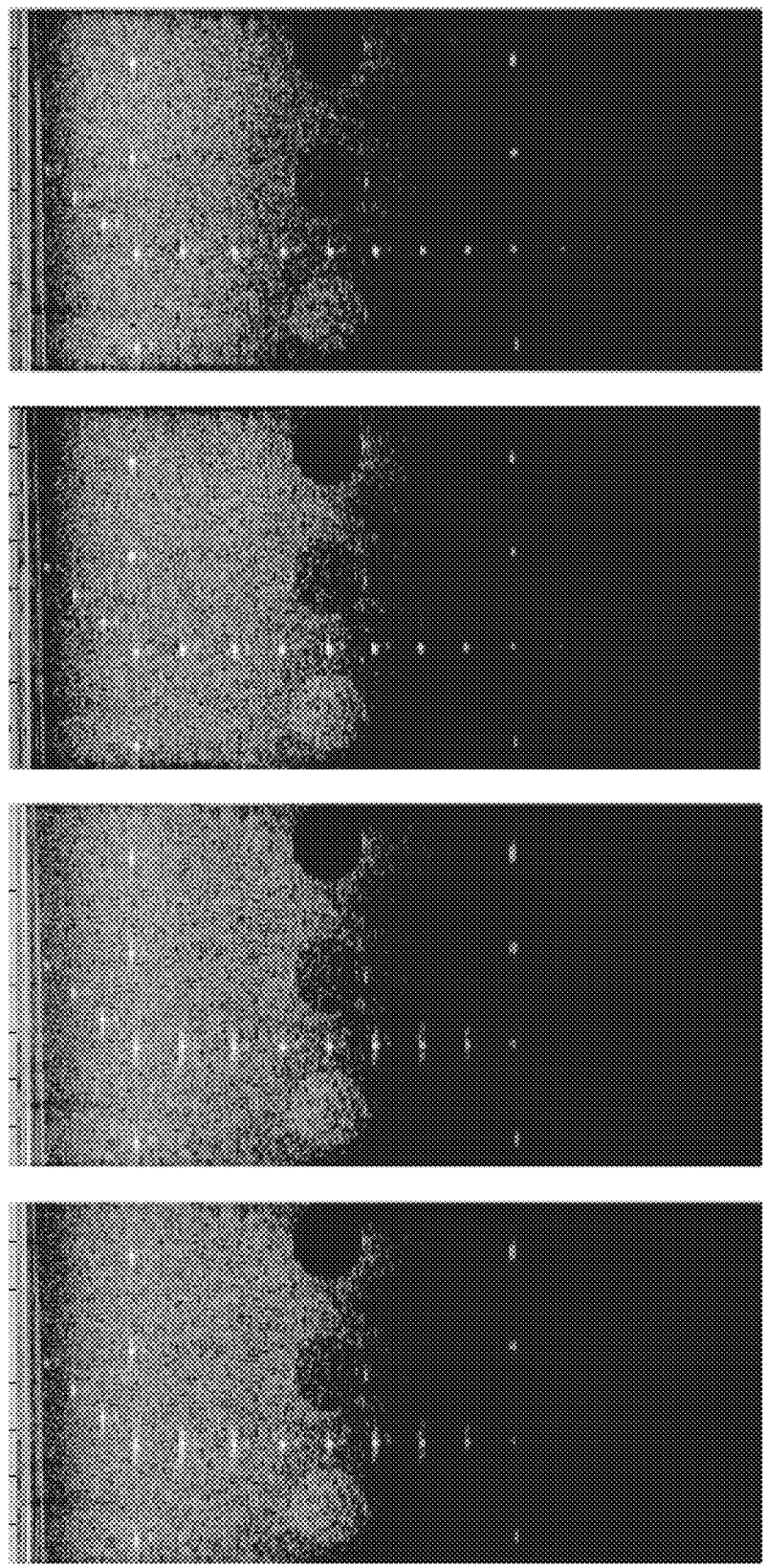

ULTRASOUND SIGNAL PROCESSING DEVICE, ULTRASOUND SIGNAL PROCESSING METHOD, AND ULTRASOUND DIAGNOSTIC DEVICE

This application is based on and claims the priority of Japanese Patent Application No. 2016-133382 filed on Jul. 5, 2016 in Japan, the contents of which are hereby incorporated by reference.

BACKGROUND OF THE INVENTION

(1) Field of the Invention

The present invention is related to an ultrasound signal processing device, and an ultrasound diagnostic device equipped with the ultrasound signal processing device. In particular, the present invention relates to receive beam forming in an ultrasound signal processing device.

(2) Description of the Related Art

Typically, an ultrasound diagnostic device transmits ultrasound towards the inside of a subject via an ultrasound probe (referred to in the following as a "probe"), and receives reflected ultrasound (an echo) via the probe. The reflected ultrasound is generated within the subject due to tissues in the subject having different acoustic impedances. Further, an ultrasound diagnostic device generates an ultrasound tomographic image based on electric signals acquired through the reception of the reflected ultrasound, and displays the ultrasound tomographic image on a monitor (referred to in the following as a "display unit"). An ultrasound tomographic image shows the structures of tissues inside the subject. Ultrasound diagnostic devices are widely used for the imaging diagnosis of subjects, for having low invasiveness and achieving real-time observation of tissues through tomographic images and the like.

A typical method applied in conventional ultrasound diagnostic devices for forming signals based on received reflected ultrasound (i.e., receive beam forming) is delay-and-sum beam forming. One example of delay-and-sum beam forming can be found disclosed in pages 42-45 of "Ultrasound Diagnostic Equipment", written by Masayasu Itou and Tsuyoshi Mochizuki and published by Corona Publishing Co., Ltd (Aug. 26, 2002). According to this method, transmission beam forming (i.e., transmission of ultrasound by a plurality of transducer elements towards the inside of the subject) is typically performed such that a transmitted ultrasound beam converges (focuses) at a predetermined focal depth inside the subject. Further, according to this method, measurement points are always set along the central axis of the transmitted ultrasound beam, as illustrated in FIG. 14A. Due to this, one ultrasound transmission event generates only one or a few acoustic line signals along the central axis of the transmitted ultrasound beam, and thus, reflected ultrasound is not utilized in an efficient manner. In addition, with this method, it is also problematic that an acoustic line signal acquired from a measurement point distant from the transmission focal point has low spatial resolution and low S/N ratio.

Meanwhile, a receive beam forming method is being proposed that utilizes a so-called synthetic aperture method to yield images with high spatial resolution and high quality not only from near the transmission focal point but also from areas other than near the transmission focal point. One example of receive beam forming utilizing the synthetic aperture method can be found disclosed in pages 395 through 405 of "Virtual Ultrasound Sources in High Resolution Ultrasound Imaging", S. I. Nikolov and J. A. Jensen, in Proc, SPIE—Progress in Biomedical Optics and Imaging, Vol. 3, 2002. According to this method, delaying is performed taking into consideration both a propagation path of ultrasound and the time amount required for reflected ultrasound to arrive at a transducer element by travelling along the propagation path. Thus, the method achieves receive beam forming making use of not only reflected ultrasound from an area of an ultrasound main irradiation area near the transmission focal point but also reflected ultrasound from areas of the ultrasound main irradiation area other than the area near the transmission focal point. Due to this, the method enables generating, from one ultrasound transmission event, acoustic line signals covering the entire ultrasound main irradiation area, including areas far from the transmission focal point. Note that in the present disclosure, an ultrasound main irradiation area is an area such that at every point in the ultrasound main irradiation area, ultrasound transmitted from transducer elements composing a transmission transducer element array is in-phase. In addition, the synthetic aperture method enables setting a virtual transmission focal point with respect to each measurement point based on multiple receive signals acquired for the same measurement point through multiple transmission events. Thus, the synthetic aperture method enables acquiring an ultrasound image with higher spatial resolution and higher S/N ratio than the receive beam forming method disclosed in "Ultrasound Diagnostic Equipment".

SUMMARY OF THE INVENTION

Problems to be Solved by the Invention

In the synthetic aperture method, for efficient use of ultrasound and high resolution, it is preferable that an area for which acoustic line signals for a single transmission event are generated (referred to in the following as a target area) have large size, and it is further preferable that the entire ultrasound main irradiation area be used as the target area. However, an increase in target area size brings about a proportional increase in the number of measurement points in the target area and an increase in computation amount for delay-and-summing taking into consideration transmission and reception delays. Due to this, an increase in target area size necessitates hardware with high computation capability to achieve high-speed delay-and-sum computation, and thus gives rise to a problem of increased ultrasound diagnostic device cost. Meanwhile, when reducing target area size by simply reducing target area width in a direction in which transducer elements are arrayed (referred to in the following as a transducer element array direction), improvement of spatial resolution and S/N ratio becomes insufficient.

The present invention has been made in view of the problems described above, and aims to provide an ultrasound signal processing device that enables reducing delay-and-sum computation amount in a synthetic aperture method utilizing converging-type transmission beam forming while suppressing decrease in spatial resolution and S/N ratio, and an ultrasound diagnostic device including the ultrasound signal processing device.

Means for Solving the Problems

One aspect of the present invention is an ultrasound signal processing device that performs multiple transmission events of transmitting converging ultrasound beams to a subject by using an ultrasound probe having multiple transducer elements, that performs, for each of the transmission events, reception of ultrasound reflection from the subject and generation of a sub-frame acoustic line signal based on the ultrasound reflection, and that combines sub-frame acoustic line signals for the respective transmission events to generate a frame acoustic line signal, the ultrasound signal processing device including ultrasound signal processing circuitry configured to operate as: a transmitter that varies a focal point defining a position where ultrasound beams converge between a plurality of transmission events and performs each of the transmission events by causing the ultrasound probe to transmit ultrasound beams directed to an inside of the subject; a receiver that, for each of the transmission events, generates sequences of receive signals for transducer elements of the ultrasound probe based on ultrasound reflection that the ultrasound probe receives from the subject; a delay-and-sum calculator that generates, for each of the transmission events, a sub-frame acoustic line signal including an acoustic line signal for each of a plurality of measurement points located on target lines that pass through the focal point and compose a target line group, the delay-and-sum calculator generating an acoustic line signal for a measurement point by performing delay-and-summing of receive signals, included in the sequences of receive signals, that are based on ultrasound reflection acquired from the measurement point; and a synthesizer that combines sub-frame acoustic line signals for the transmission events to generate a frame acoustic line signal, wherein the target lines are straight lines, and any measurement point, on any of the target lines, that is spaced away from the focal point by a predetermined distance or more satisfies a condition that a distance between the measurement point and a most nearby measurement point on the same target line is smaller than a distance between the measurement point and a most nearby one among measurement points on an adjacent target line.

Advantageous Effect of the Invention

The ultrasound signal processing device pertaining to one aspect of the present invention and an ultrasound diagnostic device including the ultrasound signal processing device are capable of reducing the number of measurement points while suppressing decrease in spatial resolution and S/N ratio of frame acoustic line signals, and thus are capable of reducing computation amount for delay-and-summing taking into consideration transmission and reception delays.

BRIEF DESCRIPTION OF THE DRAWINGS

These and the other objects, advantages and features of the invention will become apparent from the following description thereof taken in conjunction with the accompanying drawings which illustrate a specific embodiment of the invention.

FIGS. 10A and 10B are schematics pertaining to the embodiment, providing an overview of maximum overlap counts of combined acoustic line signals and amplification by an amplifier 11402;

FIGS. 15A through 15D show ultrasound images produced by receive beam forming of an implementation example and receive beam forming of the comparative examples 1 through 3.

DESCRIPTION OF EMBODIMENT

Figure 1:
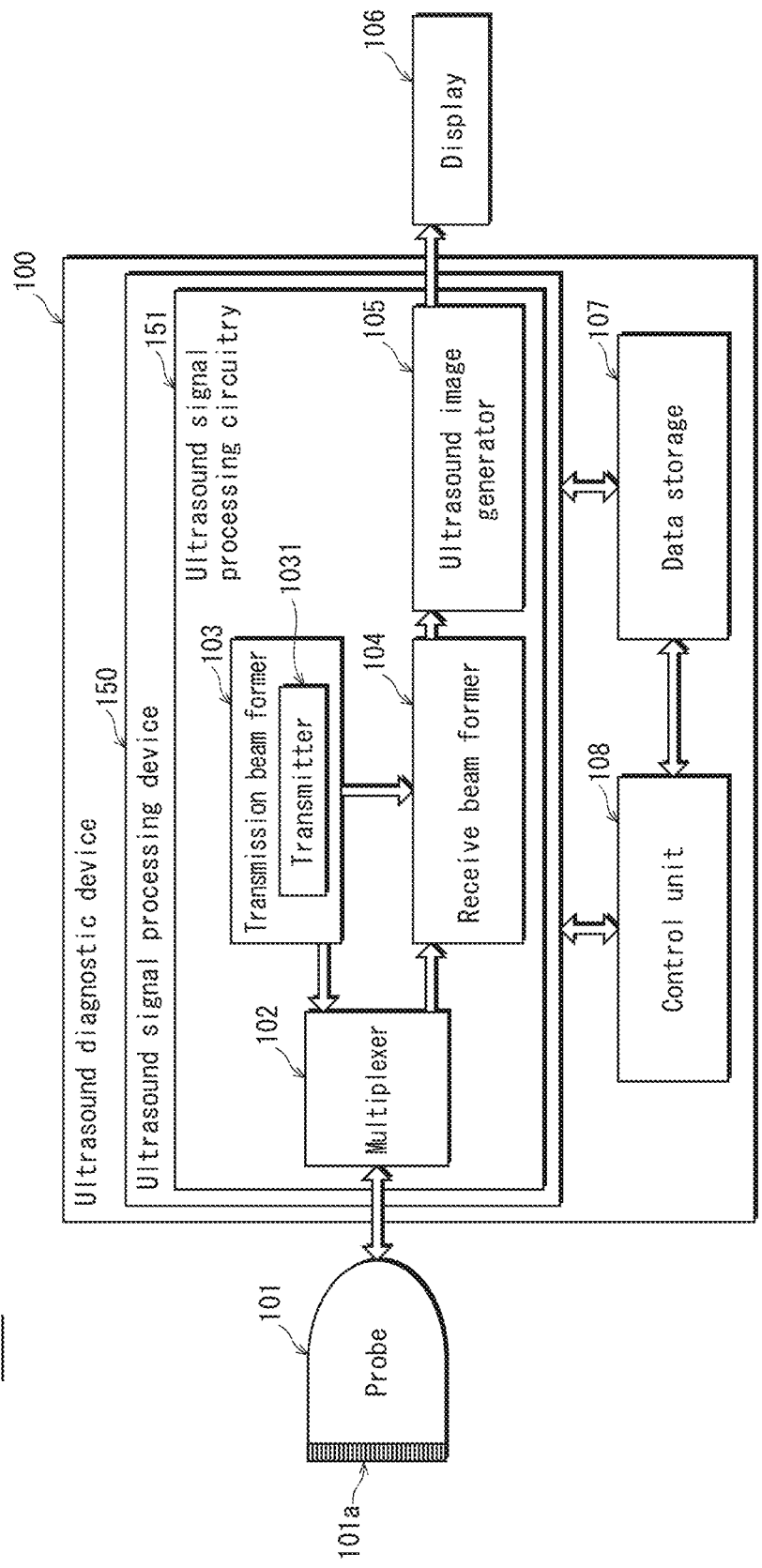
FIG. 1 is a functional block diagram illustrating the structure of an ultrasound diagnostic device 100 pertaining to an embodiment.

<How Inventor Arrived at Aspects of Present Invention>

The inventor conducted various considerations for reducing computation amount while suppressing a decrease in spatial resolution and S/N ratio of acoustic line signals (referred to in the following as acoustic line signal quality) in an ultrasound diagnostic device deploying a synthetic aperture method.

Typically, converging-type transmission beam forming is performed by causing a wavefront to converge so that an ultrasound beam focuses at a certain depth of a subject (referred to in the following as a focal depth). In each transmission of ultrasound (transmission event), transducer elements that are used for ultrasound transmission (referred to in the following as a transmission transducer element array) mainly transmit ultrasound to the ultrasound main irradiation area. For example, when ultrasound transmission is performed with one measurement point set as the transmission focal point, the ultrasound main irradiation area has an hourglass shape, the bottom edge (i.e., base) of the ultrasound main irradiation area corresponds to the transmission transducer element array, and two straight lines each extending from a different end of the base towards the transmission focal point partition the ultrasound main irradiation area from the outside thereof. Further, the wavefront of ultrasound transmitted from the transmission transducer element array forms an arc, being a segment of a circle whose center corresponds to the transmission focal point. Here, it should be noted that ultrasound beams do not always converge (i.e., focus) to a single point as described above. For example, ultrasound beams may converge to an area having a width corresponding to 1.5 times the width of a single transducer element to several times the width of a single transducer element. When ultrasound beams converge at such an area, the width of the ultrasound main irradiation area in the transducer element array direction decreases as approaching the transmission focal depth, equals the width of the transmission focal area in the transducer element array direction at the transmission focal depth, and increases in the transducer element array direction once again as departing the transmission focal depth towards deeper areas. For convenience of description, a center point of the focal area at the focal depth in such a case is referred to as a focal point. That is, regardless of whether or not ultrasound beams focus at a single point, the ultrasound main irradiation area converges, at the focal depth, at the focal point or at the focal area, which is an area including the focal point and the vicinity of the focal point. Meanwhile, at depths other than the focal depth, the greater the distance from the focal depth, the greater the width of the ultrasound main irradiation area in the transducer element array direction.

Further, with the synthetic aperture method, for each transmission event, measurement points can be set to cover the entire ultrasound main irradiation area of the transmission event. As such, it is preferable that the entirety of the ultrasound main irradiation area be set as a target area. Meanwhile, a target area for one transmission event cannot cover the entirety of an area corresponding to one frame image (referred to in the following as a region of interest (ROI)). As such, a plurality of transmission events, for each of which a different target area is set, need to be conducted to generate one frame ultrasound image. Taking this into consideration, for efficient use of ultrasound, it is preferable that a target area for a single transmission event cover as great an area of an ultrasound main irradiation area for the transmission event as possible. Further, in general, to improve spatial resolution and signal S/N ratio, it is preferable that target areas for two consecutive transmission events overlap one another as much as possible.

However, the number of measurement points included in a target area is proportional to target area size. Consequently, computation amount for delay-and-summing and the memory amount necessary to store acoustic line signals produced through the delay-and-summing are proportional to target area size. Due to this, an increase in target area size directly results in an increase in ultrasound diagnostic device memory amount required. Further, when ultrasound diagnostic device computation capability is insufficient with respect to delay-and-summing computation amount, a decrease in temporal resolution and usability may occur. This is because ultrasound diagnostic devices are not capable of achieving frame rate higher than that corresponding to their computation capability, and thus a decrease in ultrasound image frame rate may occur. Accordingly, in order to suppress such decrease in temporal resolution and usability, a processor with computation capability high enough to perform delay-and-summing computation at high speed, such as a high performance GPU, becomes necessary, which leads to an increase in ultrasound diagnostic device cost.

One measure that can be considered for reducing computation amount is reducing the number of measurement points included in the target area. Possible measures for reducing the number of measurement points include reducing target area size and reducing measurement point density in the target area. However, when reducing target area size in the depth direction, the area for which an ultrasound image can be generated decreases in proportion with target area size. Further, when reducing measurement point density in the depth direction, distance resolution, which is spatial resolution in the depth direction, decreases proportionally. Hence, the inventor sought for a method of reducing the number of measurement points in the transducer element array direction while suppressing a decrease in acoustic line signal quality, and arrived at the idea of setting, as the target area, a target line group composed of multiple target lines passing through the focal point or a focal area, and thereby reducing measurement point density transverse to target lines. By making such a configuration, the number of measurement points can be reduced without reducing the number of measurement points or the density of measurement points in the depth direction. Due to this, neither distance resolution nor the area for which an ultrasound image is generated decreases. Further, compared to reducing target area width in the transducer element array direction, this configuration suppresses decrease in resolution and S/N ratio of acoustic line signals in the depth direction, which occurs when the area of overlap between target areas for two consecutive transmission events decreases. This is because, while the number itself of overlapping measurement points between two target line groups for two consecutive transmission events decreases, the range of variations of positional relationships between a measurement point, focal points F, and a receive aperture does not decrease.

The following embodiment describes an ultrasound signal processing method and an ultrasound diagnostic device including the ultrasound signal processing method in detail, with reference to the accompanying drawings.

<Embodiment>
<Overall Structure>

The following describes an ultrasound diagnostic device 100 pertaining to the embodiment, with reference to the accompanying drawings.

FIG. 1 illustrates functional blocks of an ultrasound diagnostic system 1000 pertaining to the embodiment. As illustrated in FIG. 1, the ultrasound diagnostic system 1000 includes: a probe 101; the ultrasound diagnostic device 100; and a display unit 106. The probe 101 includes a plurality of transducer elements 101a. Each of the transducer elements 101a is capable of transmitting ultrasound towards the subject and receiving reflected ultrasound (echo signals). The ultrasound diagnostic device 100 causes the probe 101 to perform transmission/reception of ultrasound, and generates an ultrasound image based on signals output from the probe 101. The display unit 106 displays the ultrasound image on any display device provided thereto. The probe 101 and the display unit 106 are separately connectable to the ultrasound diagnostic device 100. FIG. 1 illustrates the ultrasound diagnostic device 100 with the probe 101 and the display unit 106 connected thereto. Alternatively, the ultrasound diagnostic device 100 may include therein the probe 101 and the display unit 106.

<Structure of Ultrasound Diagnostic Device 100>

The ultrasound diagnostic device 100 includes a multiplexer 102; a transmission beam former 103; and a receive beam former 104. The multiplexer 102 selects one or more of the transducer elements 101a for ultrasound transmission and one or more of the transducer elements 101a for ultrasound reception. The multiplexer 102 may select different ones of the transducer elements 101a for ultrasound transmission and ultrasound reception. Further, the multiplexer 102 provides the transducer elements 101a for ultrasound transmission with input, and receives output from the transducer elements 101a for ultrasound reception. The transmission beam former 103 controls timings of application of a high voltage for ultrasound transmission to each of the transducer elements 101a for ultrasound transmission. The receive beam former 104 performs some amplification and A/D conversion on electric signals yielded by the transducer elements 101a for ultrasound reception, based on reflected ultrasound received by the probe 101, and performs receive beam forming to generate acoustic line signals. In addition, the ultrasound diagnostic device 100 includes an ultrasound image generator 105; a data storage 107; and a control unit 108. The ultrasound image generator 105 generates an ultrasound image (a B-mode image) based on signals output from the receive beam former 104. The data storage 107 stores the acoustic line signal output from the receive beam former 104 and the ultrasound image output from the ultrasound image generator 105. The control unit 108 controls each of the other components of the ultrasound diagnostic device 100.

Among the components of the ultrasound diagnostic device 100, the multiplexer 102, the transmission beam former 103, the receive beam former 104, and the ultrasound image generator 105 constitute ultrasound signal processing circuitry 151, and the ultrasound signal processing circuit 151 constitutes an ultrasound signal processing device 150.

Each component of the ultrasound diagnostic device 100, for example, each of the multiplexer 102, the transmission beam former 103, the receive beam former 104, the ultrasound image generator 105, and the control unit 108 may be implemented by using a hardware circuit such as a field-programmable gate array (FPGA), an application-specific integrated circuit (ASIC), or the like. Alternatively, each of the components may be implemented by using a combination of software and a programmable device such as a processor. As a processor, a central processing unit (CPU) or a graphics processing unit (GPU) may be used for example, and a construction using a GPU is referred to as a General-purpose computing on graphics processing unit (GPGPU). Each of such components may be implemented as one circuit component, or as an aggregate of a plurality of circuit components. Further, a plurality of such components may be implemented by using one circuit component, or as an aggregate of a plurality of circuit components.

The data storage 107 is a computer-readable recording medium. For example, the data storage 107 may be implemented by using a flexible disk, a hard disk, an MO, a DVD, a DVD-RAM, a BD, or a semiconductor memory. Alternatively, the data storage 107 may be an external storage device connected to the ultrasound diagnostic device 100.

Note that the ultrasound diagnostic device 100 pertaining to the present embodiment need not have the structure illustrated in FIG. 1. For example, the ultrasound diagnostic device 100 may not include the multiplexer 102, and the transmission beam former 103 and the receive beam former 104 may be directly connected with each transducer element 101a of the probe 101. Further, the probe 101 may have built-in therein a part or the entirety of each of the transmission beam former 103, the receive beam former 104, and the like. Such modifications apply not only to the ultrasound diagnostic device 100 pertaining to the present embodiment, but also similarly apply to the ultrasound diagnostic devices described later in the other embodiments and modifications in the present disclosure.

<Structure of Main Part of Ultrasound Diagnostic Device 100>

The ultrasound diagnostic device 100 pertaining to the embodiment is characterized for including the transmission beam former 103 and the receive beam former 104. The transmission beam former 103 causes the transducer elements 101a of the probe 101 to transmit ultrasound. The receive beam former 104 performs computation with respect to electric signals acquired through the reception of reflected ultrasound by the probe 101, and generates acoustic line signals used in forming an ultrasound image. Accordingly, the present disclosure focuses on the structure and the functions of each of the transmission beam former 103 and the receive beam former 104. Note that components other than the transmission beam former 103 and the receive beam former 104 may have structures and functions similar to those in conventional ultrasound diagnostic devices. In other words, the ultrasound diagnostic device 100 may be implemented by replacing beam formers in a conventional ultrasound diagnostic device with the beam formers pertaining to the present embodiment.

The following describes the structure of each of the transmission beam former 103 and the receive beam former 104.

1. Transmission Beam Former 103

The transmission beam former 103 is connected to the probe 101, via the multiplexer 102. However, note that the multiplexer 102 is not a mandatory element in the present invention. The transmission beam former 103 controls timings of application of high voltage with respect to each of a plurality of transducer elements 101a composing a transmission aperture Tx. The transmission aperture Tx is an array of transducer elements composed of all or some of the transducer elements 101a of the probe 101. Note that in the following, the term "transmission transducer element" is used to refer to transducer elements composing the transmission aperture Tx. The transmission beam former 103 includes a transmitter 1031.

The transmitter 1031 performs transmission processing. The transmission processing involves supplying a transmission signal having a pulsar waveform to each of the transmission transducer elements. A transmission transducer element receiving a transmission signal transmits an ultrasound beam. The transmitter 1031 supplies transmission signals to the transmission transducer elements based on transmission control signals output from the control unit 108. In specific, the transmitter 1031 includes, for example, a clock generation circuit, a pulse generation circuit, and a delay circuit. The clock generation circuit generates a clock signal specifying the transmission timing of ultrasound beams. The pulse generation circuit generates pulse signals for driving the transmission transducer elements. The delay circuit performs focus processing so that ultrasound beams are appropriately focused. In specific, the delay circuit sets a delay time for each transmission transducer element, and delays the transmission of the ultrasound beam from the transmission transducer element by the corresponding delay time.

The transmitter 1031 repetitively performs ultrasound transmission while shifting the transmission aperture Tx in the transducer element array direction each time, so that all of the transducer elements 101a of the probe 101 transmit ultrasound. Thus, in the present embodiment, transmission apertures Tx corresponding to two consecutive transmission events differ in position in the transducer element array direction by an amount corresponding to the width of a single transducer element. Further, the transmitter 1031 outputs information indicating the positions of transmission transducer elements composing the transmission aperture Tx to the data storage 107, via the control unit 108. For example, supposing that the probe 101 has one hundred and ninety two (192) transducer elements 101a in total, the number of transmission transducer elements composing the transmission aperture Tx may be twenty (20) to one hundred (100). Further, in the present disclosure, the term transmission event is used to refer to ultrasound transmission by the transmitter 1031, performed by using one transmission aperture (i.e., one set of transmission transducer elements of the predetermined number).

Figure 2:
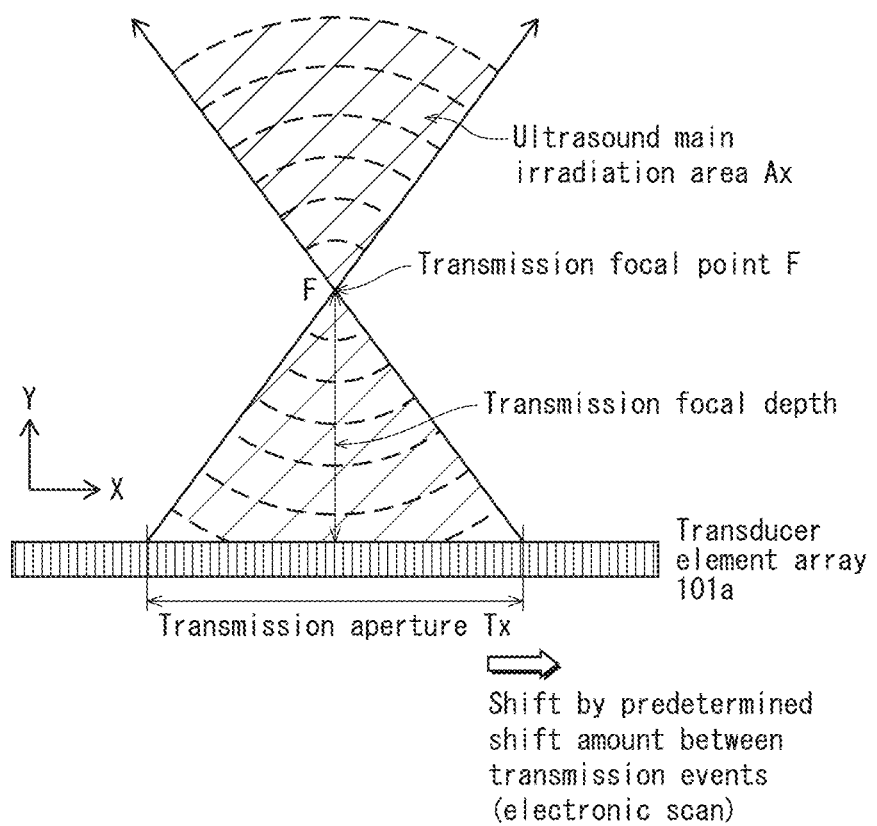
FIG. 2 is a schematic illustrating a propagation path of ultrasound transmitted from a transmission beam former 103 pertaining to the embodiment.

FIG. 2 is a schematic illustrating a propagation path of ultrasound transmitted by the transmission beam former 103. FIG. 2 illustrates a transmission aperture Tx for one transmission event (i.e., a transmission transducer element array composed of transmission transducer elements 101a that contribute to ultrasound transmission in the transmission event). Further, the transmission-array direction length of the transmission aperture Tx is considered the length of the transmission aperture Tx.

The transmission beam former 103 controls ultrasound transmission by the transmission transducer elements such that a transmission transducer element closer to the center position of the transmission aperture Tx transmits ultrasound later in the transmission event. Due to this, the wavefront of ultrasound transmitted from the transmission transducer elements composing the transmission aperture Tx converges at one point at a certain focal depth in the subject (i.e., the transmission focal point F). Note that the depth of the transmission focal point F (i.e., transmission focal depth) can be set as desired or required. After converging at the transmission focal point F, the wavefront of the transmitted ultrasound spreads out as before converging at the transmission focal point F. Thus, the transmitted ultrasound propagates through an hourglass-shaped area whose base is defined by the transmission aperture Tx and which is partitioned from other areas inside the subject by two straight lines intersecting at the transmission focal point F. More specifically, ultrasound transmitted from the transmission aperture Tx propagates in the following manner. As the transmitted ultrasound advances in a depth direction of the subject from the transmission aperture Tx, the width thereof (length along horizontal axis (X axis) in FIG. 2) gradually decreases until reaching the minimum width at the transmission focal point F. Then, as the transmitted ultrasound advances further in the depth direction from the transmission focal point F (i.e., as the ultrasound advances in the upward direction in FIG. 2), the width thereof increases (i.e., the ultrasound spreads out). In the following, the hourglass-shaped area described above is referred to as a ultrasound main irradiation area Ax. Note that as already described above, the transmission of ultrasound may be performed so that the ultrasound main irradiation area Ax converges at the focal area.

2. Receive Beam Former 104

Figure 3:
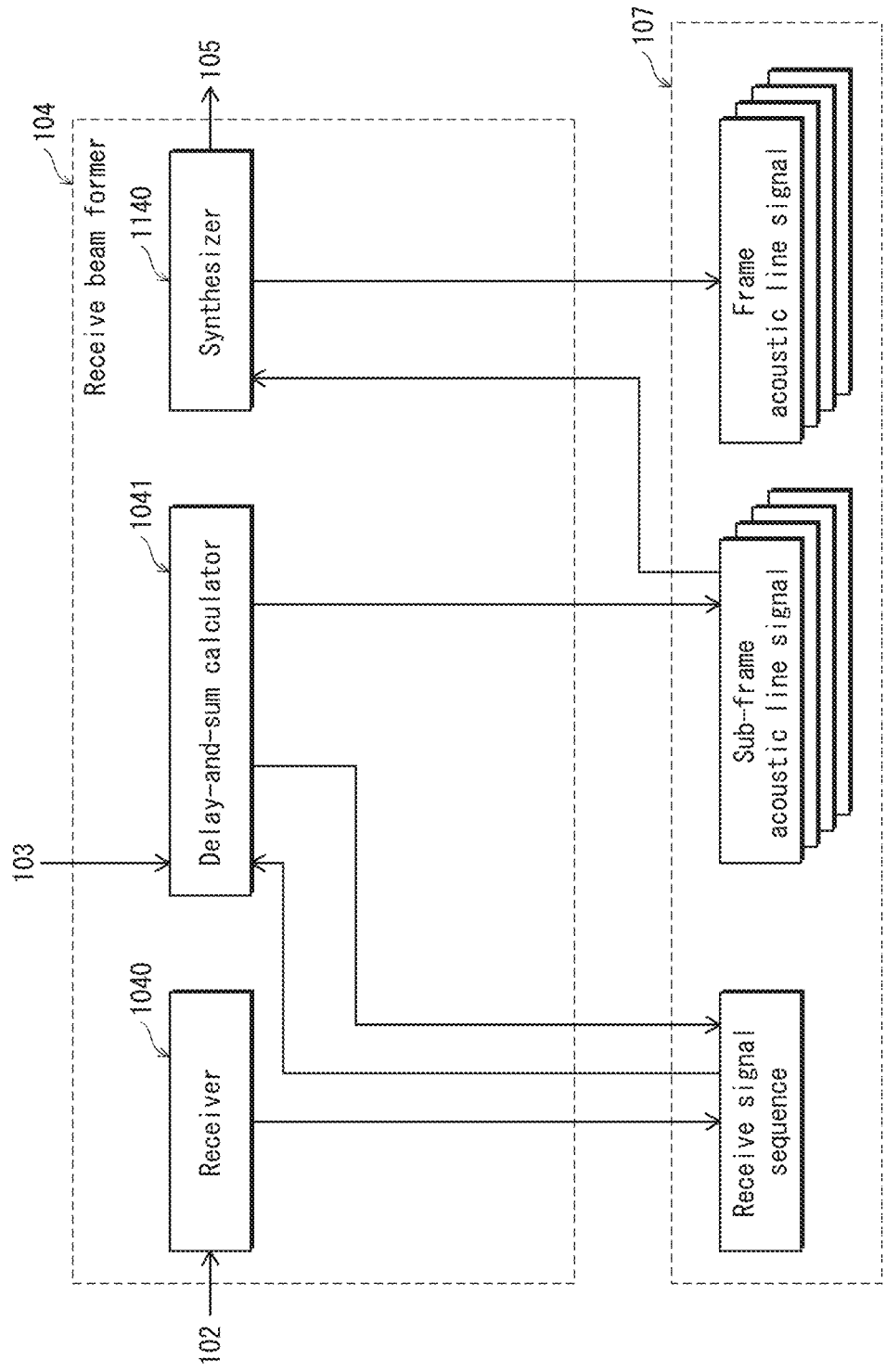
FIG. 3 is a functional block diagram illustrating the structure of a receive beam former 104 pertaining to the embodiment.

The receive beam former 104 generates acoustic line signals from electric signals acquired by a plurality of transducer elements 101a. The transducer elements 101a acquire the electric signals based on reflected ultrasound received by the probe 101. Here, an acoustic line signal for one measurement point is generated by performing delay-and-sum processing with respect to receive signals from the measurement point. Description of the delay-and-sum processing is provided later in the present disclosure. FIG. 3 is a functional block diagram illustrating the structure of the receive beam former 104. As illustrated in FIG. 3, the receive beam former 104 includes: a receiver 1040; a delay-and-sum calculator 1041; and a synthesizer 1140.

The following describes the structure of each functional block of the receive beam former 104.

(1) Receiver 1040

The receiver 1040 is connected to the probe 101, via the multiplexer 102. However, note that the multiplexer 102 is not a mandatory element in the present invention. For each transmission event, the receiver 1040 generates receive signals (RF signals). The receiver 1040 generates the receive signals by first amplifying electric signals acquired through the probe 101 receiving reflected ultrasound, and then performing A/D conversion on the amplified signals. The receiver 1040 performs the generation of receive signals for each transmission event, and outputs the receive signals to be stored in the data storage 107.

Here, the receiver 1040 generates one receive signal sequence (RF signal) for each of some or all of the transducer elements 101a of the probe 101. In specific, a receive signal sequence for a given transducer element is a digital signal yielded by performing A/D conversion on an electrical signal yielded through conversion of reflected ultrasound received by the transducer element, and is a sequence of signals along the ultrasound transmission direction (corresponding to the depth direction) that are received by the transducer element.

As discussed above, in each transmission event, the transmitter 1031 causes the plurality of transmission transducer elements composing the transmission aperture Tx, among the transducer elements 101a of the probe 101, each to transmit an ultrasound beam. Meanwhile, for each ultrasound transmission event, the receiver 1040, based on ultrasound reflection that each of some or all of the plurality of transducer elements 101a of the probe 101 acquires from the transmission event, generates a receive signal sequence for each of the transducer elements 101a having acquired the ultrasound reflection. In the present disclosure, the transducer elements 101a acquiring ultrasound reflection are referred to as "reception transducer elements". Here, it is preferable that the number of reception transducer elements be greater than the number of transmission transducer elements composing the transmission aperture Tx. Further, the number of reception transducer elements may be equal to the total number of transducer elements 101a of the probe 101.

Further, as already discussed above, the transmitter 1031 repetitively performs transmission events while shifting the transmission aperture Tx in the transducer element array direction each time, so that all of the transducer elements 101a of the probe 101 transmit ultrasound. Meanwhile, for each ultrasound transmission event, the receiver 1040 generates receive signal sequences for reception transducer elements 101a, and stores the receive signal sequences to the data storage 107.

(2) Delay-and-Sum Calculator 1041

Figure 4:
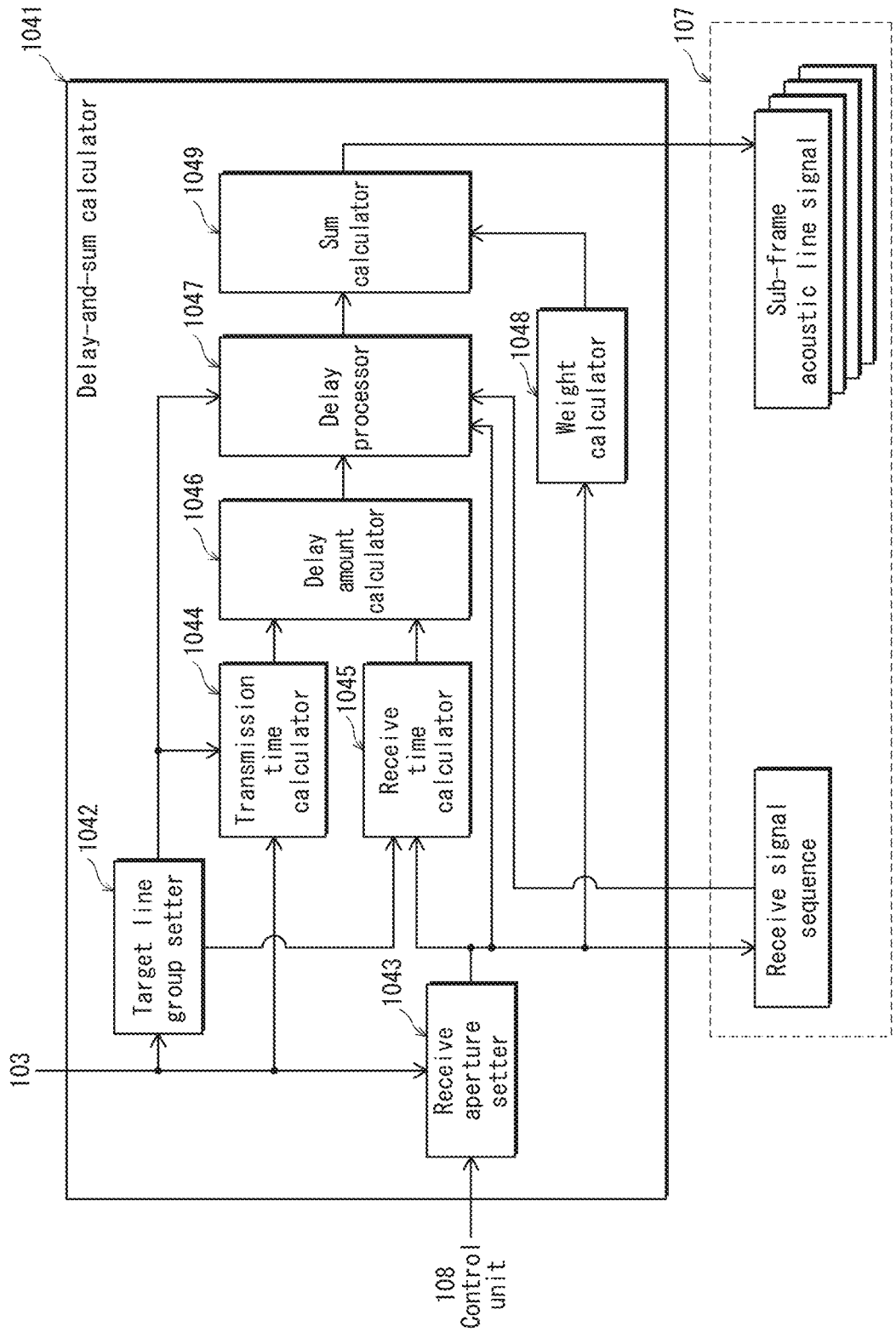
FIG. 4 is a functional block diagram illustrating the structure of a delay-and-sum calculator 1041 pertaining to the embodiment.

The delay-and-sum calculator 1041 sets a target line group Bx for each transmission event. A target line group Bx is an area in the subject from which one sub-frame acoustic line signal is to be generated, and is composed of target lines on which measurement points Pij are located. Further, the delay-and-sum calculator 1041 performs, for each measurement point Pij of the target line group Bx, delay-and-sum processing with respect to receive signal sequences corresponding to the measurement point Pij, each of which is received by one receive transducer element Rk. The delay-and-sum calculator 1041 performs this processing for each transmission event having been performed. The delay-and-sum calculator 1041, for each transmission event, generates a sub-frame acoustic line signal for the transmission event by calculating an acoustic line signal for each measurement point of the target line group Bx for the transmission event. FIG. 4 is a functional block diagram illustrating the structure of the delay-and-sum calculator 1041. As illustrated in FIG. 4, the delay-and-sum calculator 1041 includes: a target line group setter 1042; a receive aperture setter 1043; a transmission time calculator 1044; a receive time calculator 1045; a delay amount calculator 1046; a delay processor 1047; a weight calculator 1048; and a sum calculator 1049.

The following describes the structure of each functional block of the delay-and-sum calculator 1041.

i) Target Line Group Setter 1042

The delay-and-sum calculator 1042 sets the target line group Bx, which is an area in the subject from which one sub-frame acoustic line signal is to be generated. More specifically, in the present disclosure, the term "target line group" is used to indicate a signal area for generating a sub-frame acoustic line signal for one transmission event. Further, one acoustic line signal is generated for each measurement point Pij of the target line group Bx. In other words, the target line group Bx is set for each transmission event in order to specify ones of the measurement points for which acoustic line signals are to be generated for the transmission event.

Further, in the present disclosure, a sub-frame acoustic line signal is a group of acoustic lines signals that are generated from one transmission event. As already described above, from one transmission event, a plurality of acoustic line signals are generated, each for a different one of the measurement points Pij of the target line group Bx. Further, a sub-frame is a unit corresponding to a group of signals which are acquired from one transmission event and each of which corresponds to a different one of the measurement points Pij of the target line group Bx for the transmission event. Thus, a combination of multiple sub-frames acquired at different time points equals one frame.

For each transmission event, the target line group setter 1042 sets the target line group Bx based on the information indicating the position of the transmission aperture Tx for the transmission event, which is acquired from the transmission beam former 103.

Figure 5:
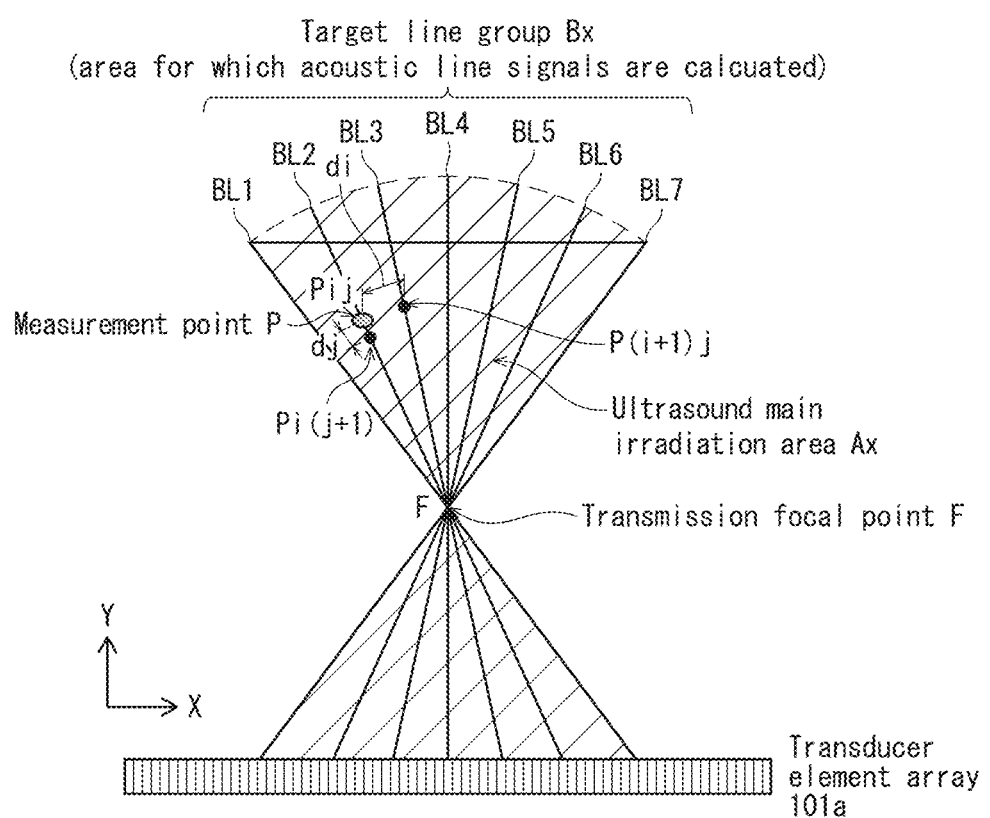
FIG. 5 is a schematic illustrating a target line group Bx pertaining to the embodiment.

FIG. 5 is a schematic illustrating one example of the target line group Bx. The target line group Bx illustrated in FIG. 5 is set inside the ultrasound main irradiation area Ax, and is composed of target lines BL1 through BL7. Each of the target lines passes through the focal point F or the focal area.

Among the target lines BL1 through BL7, target lines BL1 and BL7 each correspond to an outer boundary of the ultrasound main irradiation area Ax, and target line BL4 is located on a center axis Txo of the transmission aperture. For the sake of convenience, the following description is provided based on the assumption that the ultrasound main irradiation area Ax has two outer boundaries, one being a straight line passing through the focal point F and one end of the transmission aperture Tx, and the other being a straight line passing through the focal point F and the other end of the transmission aperture Tx. Further, every pair of adjacent ones of the target lines BL1 through BL7 form substantially the same angle therebetween. This means that measurement points on an arc centered on the focal point F are located at the same distance from one another.

Further, the following holds true for each measurement point spaced away from the focal point F by a predetermined distance or more (e.g., measurement point Pij on target line BL2): a distance dj between the measurement point Pij and an adjacent measurement point Pi(j+1) on the same target line BL2 is smaller than a distance di between the measurement point Pij and any measurement point P(i+1)j on an adjacent target line BL3. Note that distance di is at least twice the distance dj, is preferably at least four times the distance dj, and is more preferably at least eight times the distance dj. This configuration allows arranging measurement points uniformly over substantially the entirety of the ultrasound main irradiation area Ax while making measurement point density in the depth direction high and measurement point density transverse to target lines (substantially similar to the transducer element array direction and a circumferential direction of an arc centered on focal point F) low. Further, the predetermined distance referred to above indicates an area within which the distance between a measurement point on one target line and any measurement point on an adjacent target line is smaller than the distance between measurement points on the one target line. For example, supposing that the angle between adjacent target lines is θ, the predetermined distance (denoted as dp) satisfies the following equation.

$$di = 2 \times dp \times \sin(\theta/2)$$

Note that the target line group Bx need not have the shape described above. For example, points of the target lines BL1 through BL7 coming in contact with the transmission transducer element array may be spaced away at equal distance from one another. Further, while the example of the target line group Bx described above is composed of seven target lines, the number of target lines in the target line group Bx may be set to any value no smaller than three.

Further, in the example described above, measurement points Pij are located on the target lines composing the target line group Bx. However, some or all measurement points may be set at positions near (and not directly on) target lines. For example, a configuration may be made such that the measurement points Pij are located on lattice points of a Cartesian coordinate system defined using the transducer element array direction (x direction) and the depth direction (y direction) and having lattice points set along centers of transducer elements. This configuration ensures that for every measurement point Pij, there is always a transducer element with the same x coordinate, and thereby improves acoustic line signal quality. In this case, however, when attempting to set a measurement point on a target line, the target line may not pass through a lattice point at the point where the measurement point is to be set, due to the target line not necessarily being parallel to the y direction. In such a case, the measurement point is set on a lattice point near the target line, rather than directly on the target line. Here, for example, the actual coordinate position where the measurement point is to be set may be calculated by performing rounding, such as rounding half-up, at a predetermined digit with respect to the coordinate position of the measurement point on the target line.

Specifically, measurement points may be set as follows. Suppose that, in the transducer element array direction (x direction), the number of transducer elements of the ultrasound probe is 192, the position of a transducer at one end of the transducer element array is x=0, and that the position of a transducer at the other end of the transducer element array is x=191. Further, suppose that, in the depth direction, the position of the transducer element array is y=0, and that a position located deeper than the transducer element array by a width of a single transducer element is y=1. Here, when the coordinate position of the focal point F is (64, 1000), a target line set to pass through coordinate position (31, 0) can be expressed by using the following mathematical expression.

$$y=(1000/33)\times(x-31)$$

Here, when trying to set a measurement point at a depth of y=1500, the coordinate position of the measurement point would be (80.5, 1500). However, according to the above configuration, the measurement point may be actually set at coordinate position (81, 1500). This allows performing delay-and-summing based on the transducer element located at x=81, and thereby improves acoustic line signal quality. Note that the setting of the actual measurement point position need not be performed as described above, and may performed in any way as long as a measurement point on a target line of the target line group Bx is actually set at a nearby point calculated by performing rounding with respect to the coordinate value of the measurement point.

The target line group setter 1042 outputs the target line group Bx to the receive aperture setter 1043, the transmission time calculator 1044, the receive time calculator 1045, and the delay processor 1047.

ii) Receive Aperture Setter 1043

The receive aperture setter 1043 is a circuit that sets, for each transmission event, receive apertures Rx based on a control signal from the control unit 108 and information from the target line group setter 1042 indicating the target line group Bx for the transmission event. In specific, the receive aperture setter 1043 selects, for each measurement point Pij of the target line group Bx, some of the transducer elements 101*a* of the probe 101 as receive transducer elements forming a transducer element array (referred to in the following as a receive transducer element array) whose center position corresponds to a transducer element Xk spatially closest to the measurement point Pij.

Figure 6:
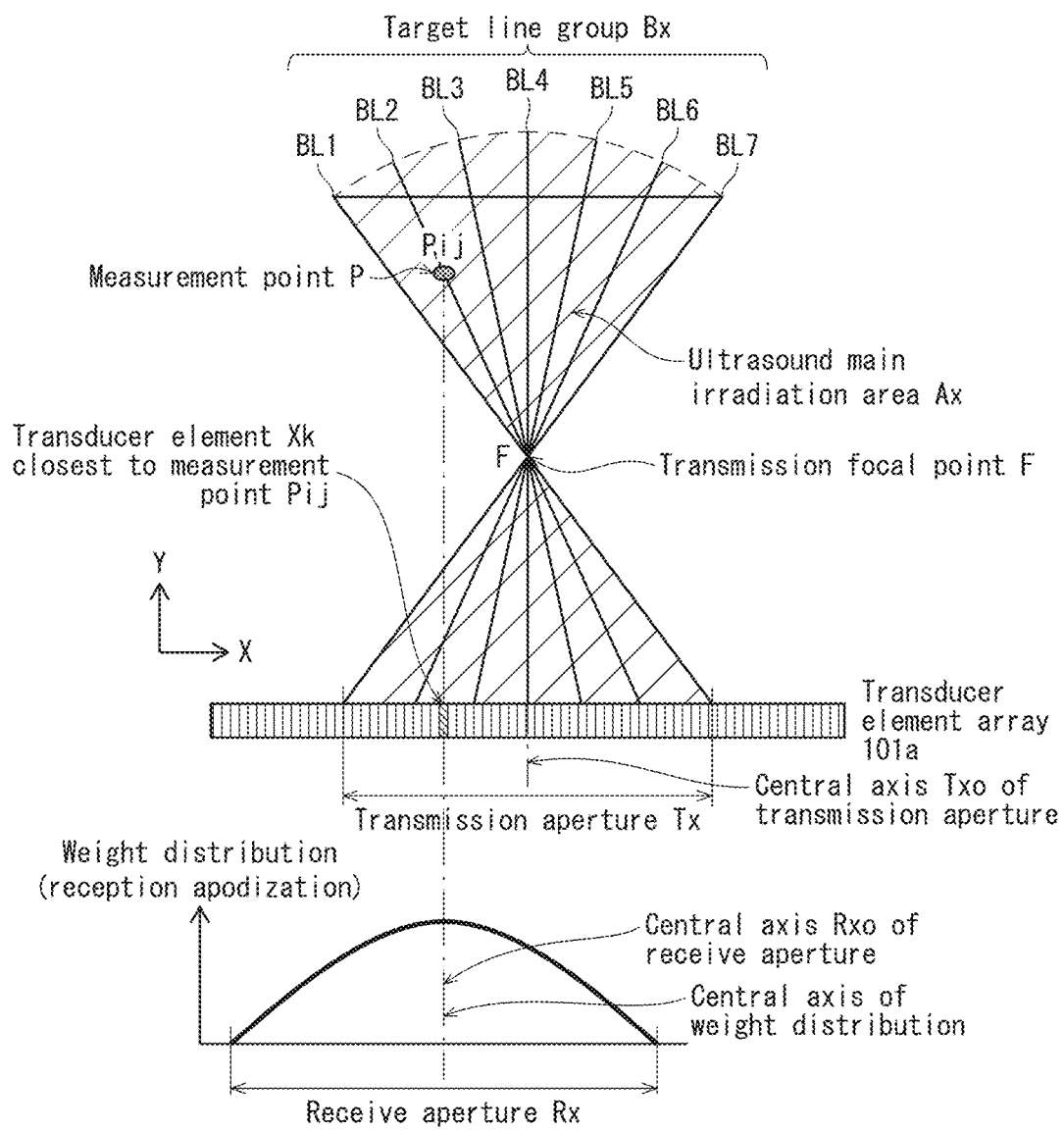
FIG. 6 is a schematic illustrating the relationship between a transmission aperture Tx and a receive aperture Rx set by a receive aperture setter 1043 pertaining to the embodiment.

The receive aperture setter 1043 sets, for each measurement point Pij of the target line group Bx for a transmission event, a receive aperture Rx (i.e., the receive transducer element array) so that the center position of the receive aperture Rx in the transducer element array direction corresponds to a transducer element Xk that is spatially closest to the measurement point Pij. FIG. 6 is a schematic illustrating the relationship between a transmission aperture Tx and a receive aperture Rx that the receive aperture setter 1043 sets. As illustrated in FIG. 6, for a given measurement point Pij, the receive aperture Rx is set so that the center position of the receive aperture Rx in the transducer element array direction corresponds to a transducer element Xk that is spatially closest to the measurement point Pij. Due to this, the position of the receive aperture Rx depends upon the position of the measurement point Pij, and does not change depending upon the position of the transmission aperture Tx, which shifts each time a transmission event is performed. That is, delay-and-sum processing for generating an acoustic line signal for a given measurement point Pij is always performed based on receive signal sequences acquired by receive transducer elements Rk composing the same receive aperture Rx. This means that with respect to the measurement point Pij, the same receive aperture Rx is used in delay-and-sum processing irrespective of transmission events.

In order to utilize reflected ultrasound from the entirety of the ultrasound main irradiation area, the number of the receive transducer elements composing each receive aperture Rx is, beneficially, greater than or equal to the number of transmission transducer elements composing each transmission aperture Tx. For example, the number of receive transducer elements may be 32, 64, 96, 128, 192, and so on.

The setting of the receive apertures Rx is performed at least for each transmission event. Due to this, the setting of the receive apertures Rx is repeated at least for the number of times transmission events are performed. Further, the setting of receive apertures Rx may be performed each time a transmission event is performed as described above, or alternatively, receive apertures Rx for multiple transmission events having been performed may be set at once after the completion of the transmission events.

Further, the receive aperture setter 1043 outputs information indicating the positions of the receive transducer elements composing the receive aperture Rx to the data storage 107, via the control unit 108.

The data storage 107 outputs the information indicating the positions of the receive transducer elements composing the receive aperture Rx along with receive signal sequences for the receive transducer elements to each of the transmission time calculator 1044, the receive time calculator 1045, the delay processor 1047, and the weight calculator 1048.

iii) Transmission Time Calculator 1044

The transmission time calculator 1044 is a circuit that, for each transmission event, calculates a transmission time for each measurement point P of the target line group Bx for the transmission event. The transmission time for a given measurement point P is the time amount required for transmitted ultrasound to arrive at the measurement point P. The transmission time calculator 1043 acquires information indicating the positions of the transmission transducer elements for a given transmission event from the data storage 107, and information indicating the position of the target line group Bx for the transmission event, which includes the ultrasound main irradiation area Ax, from the target line group setter 1042. Based on such information, the transmission time calculator 1043, for each measurement point Pij located on the target lines composing the target line group Bx, calculates the transmission time required for transmitted ultrasound to arrive at the measurement point Pij.

Figure 7A:
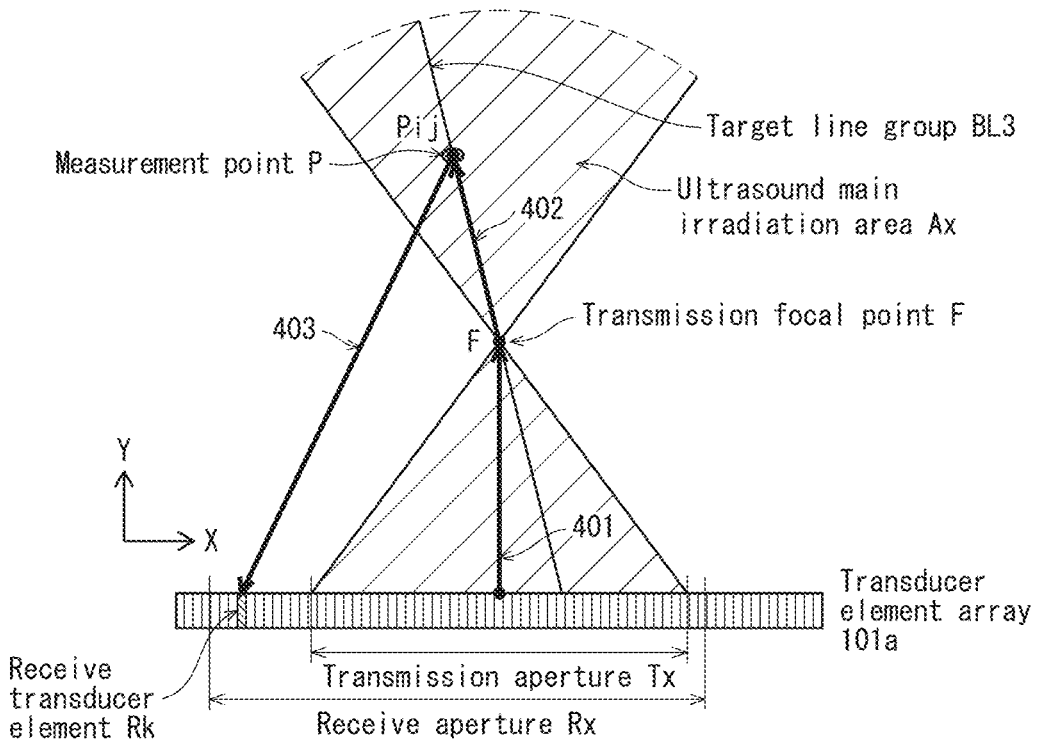
FIG. 7A is a schematic pertaining to the embodiment, illustrating one propagation path of ultrasound that is transmitted from the transmission aperture Tx and arrives at a receive transducer element Rk via a measurement point Pij.
Figure 7B:
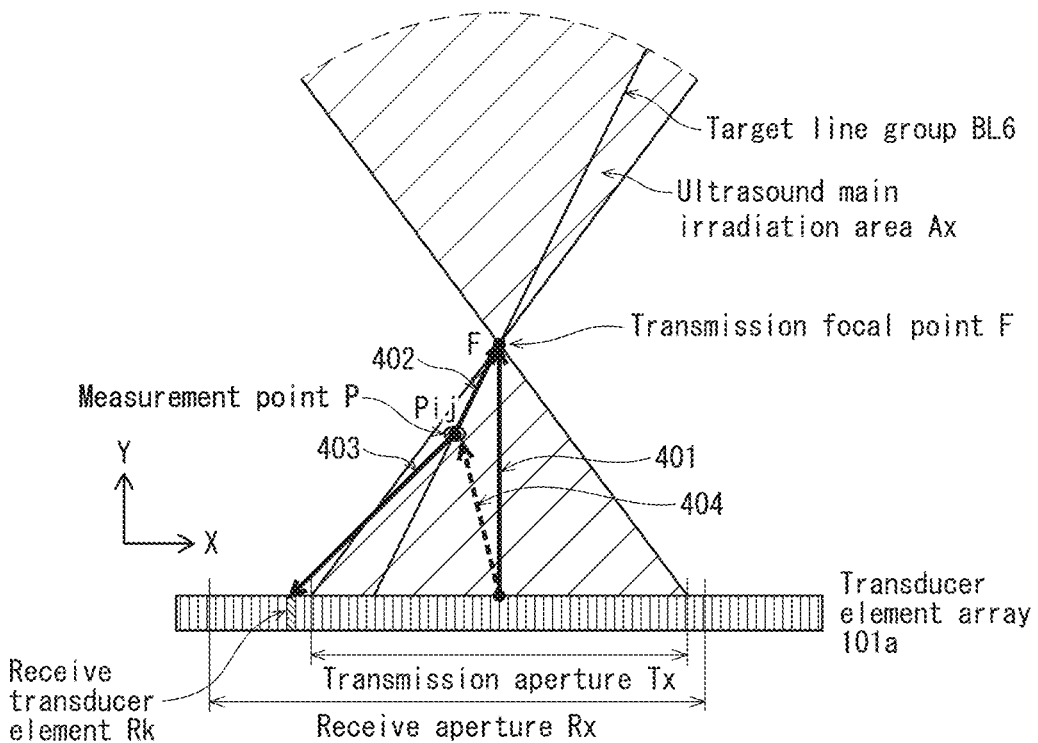
FIG. 7B is a schematic pertaining to the embodiment, illustrating another propagation path of ultrasound that is transmitted from the transmission aperture Tx and arrives at a receive transducer element Rk via a measurement point Pij.

Each of FIGS. 7A and 7B is a schematic illustrating a propagation path of ultrasound that is transmitted from the transmission aperture Tx for a transmission event, is then reflected at a measurement point Pij of the target line group Bx for the transmission event, and finally arrives at a receive transducer element Rk of the receive aperture Rx. Specifically, FIG. 7A illustrates the propagation path of ultrasound for a measurement point Pij located deeper than the transmission focal depth, whereas FIG. 7B illustrates the propagation path of ultrasound for a measurement point Pij located shallower than the transmission focal depth. Note that when comparing the position of a measurement point Pij located deeper than the transmission focal depth and the position of a measurement point Pij located shallower than the transmission focal depth, the measurement point Pij located deeper than the transmission focal depth is located relatively far from the probe and the measurement point Pij located shallower than the transmission focal depth is located relatively near to the probe.

Following emission of ultrasound from the transmission aperture Tx, the wavefront of ultrasound converges at the transmission focal point F after proceeding along the path 401. Subsequently, the wavefront spreads out once again and arrives at the measurement point Pij. When there is a change in acoustic impedance at the measurement point Pij, transmitted ultrasound generates ultrasound reflection, which is received by the receive transducer elements Rk of the receive aperture Rx. The transmission focal point F is preset in advance upon designing of the transmission beam former 103. Thus, the length of the path 402 from the transmission focal point F to the measurement point Pij can be calculated geometrically.

The following describes how the transmission time is calculated in further detail.

First, the calculation of a transmission time for a measurement point Pij located deeper than the transmission focal depth is described, with reference to FIG. 7A. A transmission time for a measurement point Pij located deeper than the transmission focal depth is calculated assuming that ultrasound transmitted from the transmission aperture Tx arrives at the transmission focal point F by traveling along path 401, and then arrives at the measurement point Pij by traveling along path 402 from the transmission focal point F. As such, the transmission time for such a measurement point Pij is the total of the time amount required for transmitted ultrasound to travel through path 401 and the time amount required for transmitted ultrasound to travel through path 402. Specifically, the transmission time for such a measurement point Pij can be calculated, for example, by dividing the total of the lengths of paths 401 and 402 by the velocity at which ultrasound propagates within the subject.

In the meantime, the following describes the calculation of a transmission time for a measurement point Pij located shallower than the transmission focal depth, with reference to FIG. 7B. A transmission time for a measurement point Pij located shallower than the transmission focal depth is calculated assuming that the time amount required for ultrasound transmitted from the transmission aperture Tx to arrive at the transmission focal point F by travelling along path 401 equals the time amount required for ultrasound transmitted from the transmission aperture Tx to travel along path 404 to arrive at the measurement point Pij and then travel along path 402 to arrive at the transmission focal point F from the measurement point Pij. As such, the transmission time for such a measurement point Pij is calculated by subtracting the time amount required for transmitted ultrasound to travel through the path 402 from the time amount required for transmitted ultrasound to travel through the path 401. Specifically, a transmission time for such a measurement point Pij can be calculated, for example, by dividing the value acquired by subtracting the length of path 401 from the length of path 401, by the velocity at which ultrasound propagates within the subject.

Note that in the present embodiment, a transmission time for a measurement point Pij located at the transmission focal depth is calculated in the same way as the transmission time for a measurement point Pij located deeper than the transmission focal depth. That is, a transmission time for a measurement point Pij located at the transmission focal depth is calculated by using the total of the time amount required for transmitted ultrasound to travel through path 401 and the time amount required for transmitted ultrasound to travel through path 402. Alternatively, a transmission time for a measurement point Pij located at the transmission focal depth may be calculated in the same way as the transmission time for a measurement point Pij located shallower than the transmission focal depth, or that is by using a value obtained by subtracting the time amount required for transmitted ultrasound to travel through the path 402 from the time amount required for transmitted ultrasound to travel through the path 401. This is because the length of the path 402 is zero in this case, and thus, the transmission time for a measurement point Pij located at the transmission focal depth equals the time amount required for transmitted ultrasound to travel through path 401 with either calculation method.

For each transmission event, the transmission time calculator 1044 calculates the transmission time for each measurement point Pij of the target line group Bx for the transmission event. That is, the transmission time calculator 1044 calculates, for each measurement point Pij, the time amount required for transmitted ultrasound to arrive at the measurement point Pij. Further, the transmission time calculator 1044 outputs the transmission time so calculated to the delay amount calculator 1046.

iv) Receive Time Calculator 1045

The receive time calculator 1045 is a circuit that calculates, for each measurement point P, a receive time required for ultrasound reflection from the measurement point P to arrive at each receive transducer element Rk of the receive aperture Rx. For a given transmission event, the receive time calculator 1045 acquires information indicating the positions of the receive transducer elements Rk for the given transmission event from the data storage 107, and acquires the information indicating the position of the target line group Bx for the given transmission event from the target line group setter 1042. Based on such information, the receive time calculator 1045, for each measurement point Pij of the target line group Bx, calculates the receive time required for transmitted ultrasound to arrive at each receive transducer element Rk after being reflected at the measurement point Pij.

As already discussed above, transmitted ultrasound arriving at a measurement point Pij generates ultrasound reflection when there is a change in acoustic impedance at the measurement point Pij. The reflected ultrasound is then received by receive transducer elements Rk of the receive aperture Rx. As discussed above, the receive time calculator 1045 acquires information indicating the positions of the receive transducer elements Rk of the receive aperture Rx from the data storage 107. Accordingly, the receive time calculator 1045 is able to geometrically calculate the length of paths 403 leading from the measurement point Pij to the respective receive transducer elements Rk.

For each transmission event, the receive time calculator 1045 calculates the receive time for each measurement point Pij of the target line group Bx for the transmission event. That is, the receive time calculator 1045 calculates, for each measurement point Pij, the time required for transmitted ultrasound to arrive at each receive transducer element Rk after being reflected at the measurement point Pij. Further, the receive time calculator 1045 outputs the receive time so calculated to the delay amount calculator 1046.

v) Delay Amount Calculator 1046

The delay amount calculator 1046 is a circuit that calculates, for each receive transducer element Rk, a total propagation time based on the transmission time and the receive time for the receive transducer element Rk. Further, the delay amount calculator 1046 calculates, for each receive transducer element Rk, a delay amount to be applied to a receive signal sequence for the receive transducer element Rk. In specific, the delay amount calculator 1046 acquires, from the transmission time calculator 1044, the transmission time required for ultrasound waves to arrive at a measurement point Pij. Further, for each receive transducer element Rk, the delay amount calculator 1046 acquires, from the receive time calculator 1045, the receive time required for ultrasound to be reflected at the measurement point Pij and arrive at the receive transducer element Rk. Then, the delay amount calculator 1046, for each receive transducer Rk, calculates a total propagation time required for transmitted ultrasound to arrive at the receive transducer element Rk. Further, based on the difference between total propagation times for the receive transducer elements Rk, the delay amount calculator 1046 calculates a delay amount for each receive transducer element Rk. For each measurement point P of the target line group Bx, the delay amount calculator 1046 calculates, for each receive transducer element Rk, the delay amount to be applied to a receive signal sequence for the receive transducer element Rk, and outputs the delay amounts to the delay processor 1047.

vi) Delay Processor 1047

The delay processor 1047 is a circuit that specifies, for each receive transducer element Rk, a receive signal based on reflected ultrasound from a measurement point Pij. In specific, for each receive transducer element Rk, the delay processor 1047 specifies a receive signal corresponding to the delay amount for the receive transducer element Rk from the receive signal sequence for the receive transducer element Rk.

More specifically, for each transmission event, the delay processor 1047 acquires, for each receive transducer element Rk, information indicating the position of the receive transducer element Rk from the receive aperture setter 1043, the receive signal sequence for the receive transducer element Rk from the data storage 107, and the delay amount to be applied to the receive signal sequence of the receive transducer element Rk from the delay amount calculator 1046. In addition, for each transmission event, the delay processor 1047 acquires the information indicating the position of the target line group Bx from the target line group setter 1042. Further, for each receive transducer element Rk, the delay processor 1047 specifies a receive signal based on reflected ultrasound from a measurement point Pij. In specific, the delay processor 1047 specifies, from the receive signal sequence for the receive transducer element Rk, a receive signal corresponding to a time point after subtraction of the delay amount for the receive transducer element Rk. The delay processor 1047 outputs the receive signal so specified to the sum calculator 1049.

vii) Weight Calculator 1048

The weight calculator 1048 is a circuit that calculates a weight sequence (reception apodization weight) for the receive transducer elements Rk, so that the maximum weight is set with respect to the receive transducer element located at the center of the receive aperture Rx in the transducer element array direction.

As illustrated in FIG. 6, the weight sequence is a numerical sequence of weight coefficients that are to be applied to receive signals for the receive transducer elements composing the receive aperture Rx. The weight sequence indicates weights that are distributed symmetrically with respect to the measurement point Pij. As the shape of distribution of the weights indicated by the weight sequence, any shape is applicable, including but not limited to a hamming window, a hanning window, and a rectangular window. The weight sequence is set so that the maximum weight is set with respect to the receive transducer element located at the center position of the receive aperture Rx in the transducer element array direction, and the central axis of the weight distribution corresponds to the center axis Rxo of the receive aperture Rx. The weight calculator 1048 uses as input information indicating the positions of the receive transducer elements Rk, which is output from the receive aperture setter 1043, and outputs the weight sequence for the receive transducer elements Rk to the sum calculator 1049.

viii) Sum Calculator 1049

The sum calculator 1049 is a circuit that generates a delayed-and-summed acoustic line signal for each measurement point P, by using as input the specified receive signals for the receive transducer elements Rk, which are output from the delay processor 1047, and summing together the specified receive signals. Alternatively, the sum calculator 1049 may generate an acoustic line signal for each measurement point P by using as input the weight numerical sequence for the receive transducer elements Rk, which is output from the weighting calculator 1048, multiplying the specified receive signal for each receive transducer element Rk with a corresponding weight, and summing the weighted receive signals. The sum calculator 1049 sums the receive signals for the receive transducer elements Rk, after the receive signals have been put in the same phase by the delay processor 1047. Due to this, the sum calculator 1049 is capable of increasing the S/N ratio of the receive signals received by the receive transducer elements Rk based on reflected ultrasound from the measurement point Pij, and receive signals for the measurement point Pij can be extracted.

As a result of one transmission event and processing accompanying the transmission event, an acoustic line signal is generated for each measurement point P of the target line group Bx for the transmission event. Further, by repetitively performing transmission events while shifting the transmission aperture Tx in the transducer element array direction each time, all of the transducer elements 101a in the probe 101 perform ultrasound transmission. Due to this, a frame acoustic line signal, which is a combination of acoustic line signals corresponding to one frame, is generated.

In the present embodiment, acoustic line signals for respective measurement points, which compose the frame acoustic line signal and each of which is generated by combining a plurality of acoustic lines signals corresponding to the measurement point that are included in different sub-frame acoustic line signals, are each referred to as a combined acoustic line signal for the measurement point.

The sum calculator 1049, for each transmission event, generates a sub-frame acoustic line signal being a combination of acoustic line signals for every measurement point Pij of the target line group Bx for the transmission event. Further, the sum calculator 1049 outputs the sub-frame acoustic line signals so generated to be stored in the data storage 107.

(5) Synthesizer 1140

Figure 8:
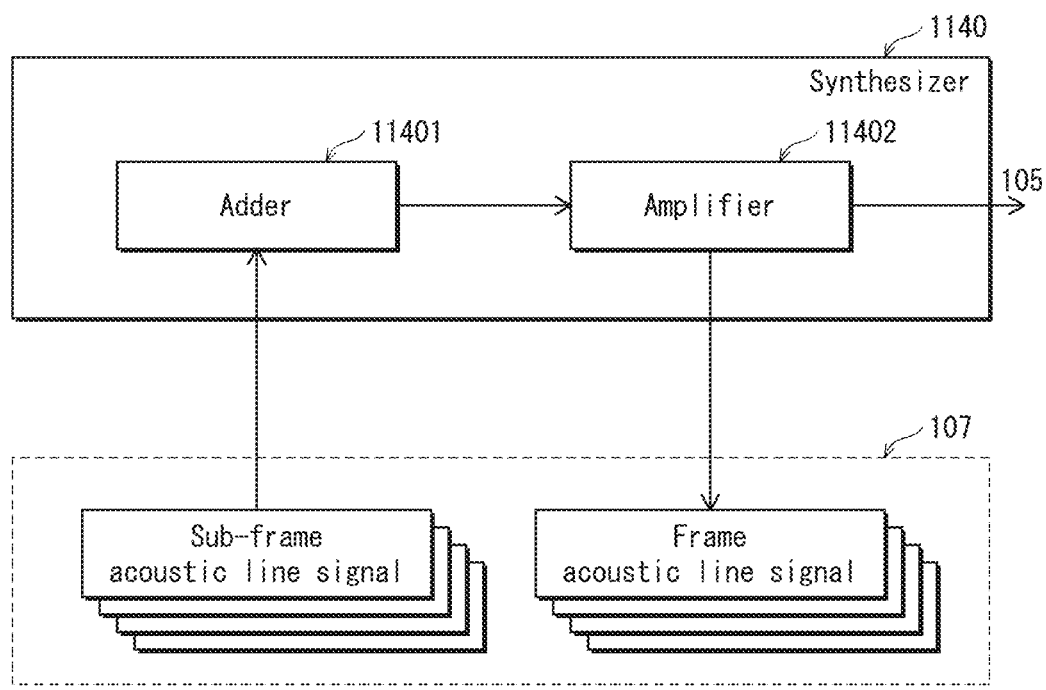
FIG. 8 is a functional block diagram illustrating the structure of a synthesizer 1140 pertaining to the embodiment.

The synthesizer 1140 is a circuit that generates a frame acoustic line signal by combining a plurality of sub-frame acoustic line signals each generated for one transmission event. FIG. 8 is a functional block diagram illustrating the structure of the synthesizer 1140. As illustrated in FIG. 8, the synthesizer 1140 includes an adder 11401 and an amplifier 11402.

The following describes the structure of each functional block of the synthesizer 1140.

i) Adder 11401

The adder 11401, after the generation of a series of sub-frame acoustic line signals necessary for generating one frame acoustic line signal is completed, reads out the sub-frame acoustic line signals from the data storage 107. Further, the adder 11401 generates a frame acoustic line signal by combining the plurality of sub-frame acoustic line signals. The combining of the sub-frame acoustic line signals is performed according to the positions of the measurement points Pij, such that in the process, a combined acoustic line signal is generated for each measurement point Pij. In specific, the adder 11401 generates a combined acoustic line signal for a given measurement point Pij by combining a plurality of acoustic line signals corresponding to the measurement point Pij that are included in different sub-frame acoustic line signals. Due to this, acoustic line signals for the same measurement point that are included in different sub-frame acoustic line signals are combined, to generate a combined acoustic line signal for the measurement point.

Figure 9:
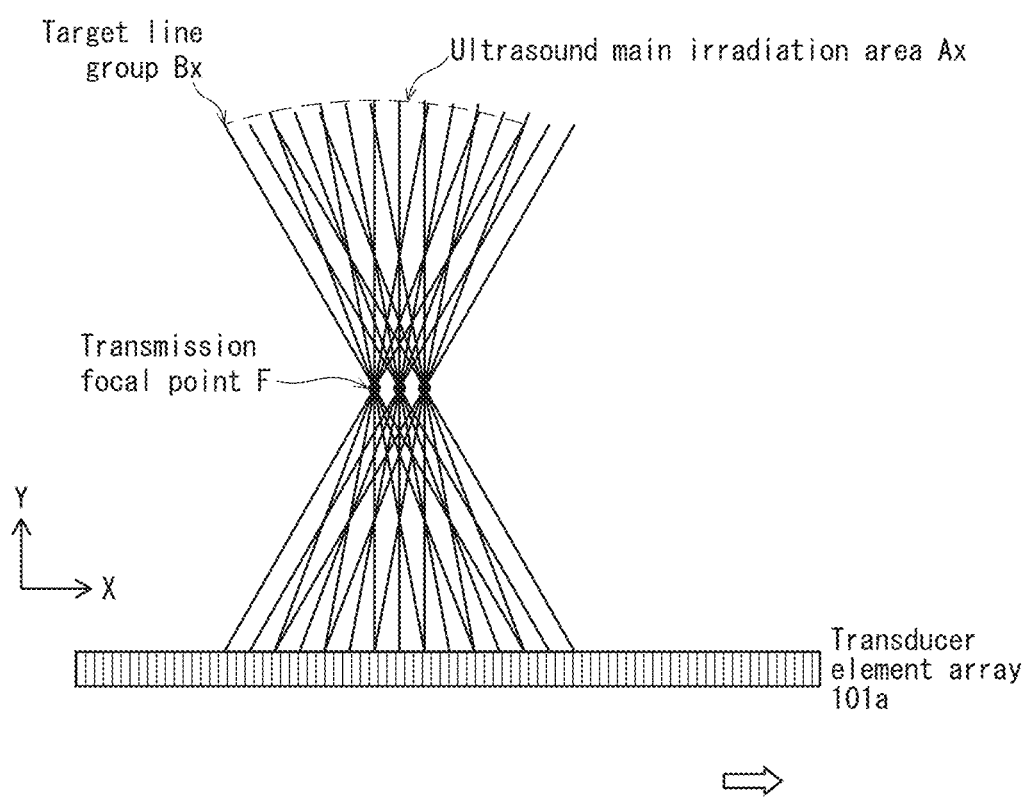
FIG. 9 is a schematic illustrating processing by an adder 11401 pertaining to the embodiment for generating a combined acoustic line signal.

FIG. 9 is a schematic illustrating processing by the adder 11401 for generating a combined acoustic line signal. As already discussed above, ultrasound transmission is performed by repetitively performing transmission events while shifting the transmission transducer element array (i.e., the transmission aperture Tx) in the transducer element array direction each time. Due to this, target line groups Bx for two consecutive transmission events differ in position from one another in the transducer element array direction by a width of a single transducer element. Thus, a frame acoustic line signal covering all target line groups Bx can be generated by combining sub-frame acoustic line signals based on the positions of the measurement points Pij from which the acoustic lines signals included in the sub-frame acoustic line signals are acquired.

Further, for a measurement point included in multiple target line groups Bx, values of a plurality of acoustic line signals included in different sub-frame acoustic line signals are summed. Thus, the combined acoustic line signal for such a measurement point may indicate a great value, depending upon the number of target line groups Bx in which the measurement point is included. In the following, the number of different target line groups Bx in which a given measurement point is included is referred to as an overlap count of the measurement point, and the maximum value of the overlap count in the transducer element array direction is referred to as a maximum overlap count.

Further, in the present embodiment, the target line group Bx has an hourglass-shape. Due to this, the overlap count and the maximum overlap count fluctuate in the depth direction of the subject, as illustrated in FIG. 10A. Accordingly, there is a depth-direction fluctuation in values of combined acoustic line signals. However, when the total number of target line groups is eleven for example, the maximum overlap count is consequently limited to eleven at most in the present embodiment.

Note that in combining sub-frame acoustic line signals based on the positions of the measurement points Pij from which the acoustic lines signals included in the sub-frame acoustic line signals are acquired to generate combined acoustic line signals for the respective measurement points, the adder 11401 may add weights in accordance with the positions of the measurement points Pij.

The adder 11401 outputs the frame acoustic line signal so generated to the amplifier 10492.

ii) Amplifier 11402

As already described above, there is a depth-direction fluctuation in values of combined acoustic line signals. In order to moderate such fluctuation in values of different combined acoustic line signals, the amplifier 11402, in combining the combined acoustic line signals to generate the frame acoustic line signal, performs amplification of multiplying the combined acoustic line signals by amplification factors. Here, the amplifier 11402 determines an amplification factor for a given combined acoustic line signal according to the number of acoustic line signals combined to yield the combined acoustic line signal.

FIG. 10B is a schematic providing an overview of the amplification performed by the amplifier 11402. The maximum overlap count fluctuates in the depth direction, as illustrated in FIG. 10B. Thus, to compensate with this fluctuation in maximum overlap count, the amplifier 11402 multiplies the combined acoustic line signals by respective amplification factors that are based on the maximum overlap counts and vary in the depth direction, as illustrated in FIG. 10B. This moderates a difference between values of combined acoustic line signals deriving from the fluctuation in overlap counts in the depth direction, and thus, the values of the combined acoustic line signals after the amplification are averaged out in the depth direction. That is, the amplification performed by the amplifier 11402 is gain equalization in the depth direction.

Further, the amplifier 11402 may also multiply the combined acoustic line signals by amplification factors varying in the transducer element array direction that are calculated based on overlap counts, when overlap counts fluctuate in the transducer element array direction. This moderates a difference between values of combined acoustic line signals deriving from the fluctuation in overlap counts in the transducer element array direction, and thus, the values of the combined acoustic line signals after the amplification are averaged out in the transducer element array direction.

Here, note that the amplifier 11402 may generate the frame acoustic line signal by combining amplified combined acoustic line signals for respective measurement points.

<Operations>

The following describes the operations of the ultrasound diagnostic device 100 having the structure described up to this point.

Figure 11:
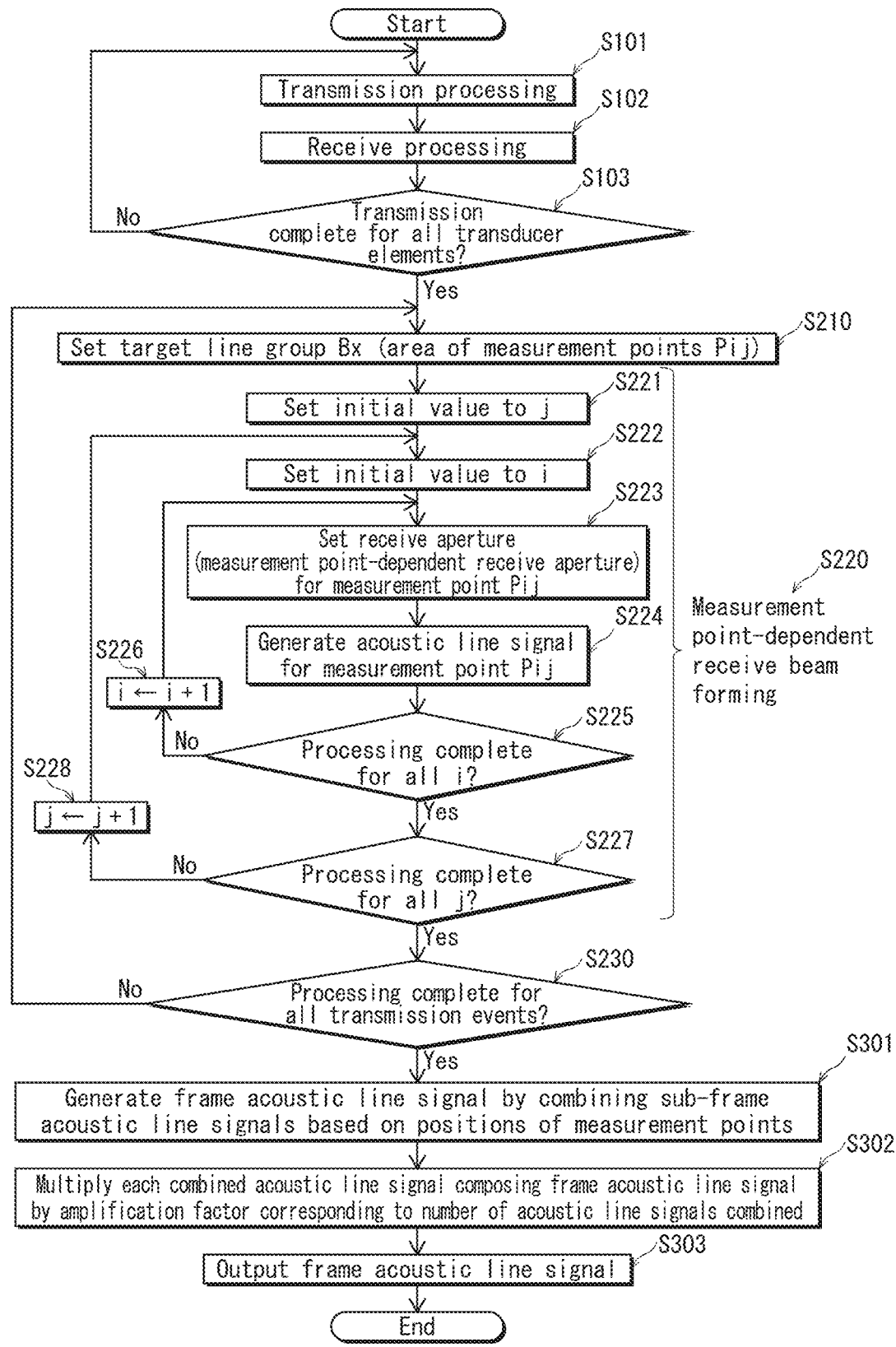
FIG. 11 is a flowchart illustrating beam forming by the receive beam former 104 pertaining to the embodiment.

FIG. 11 is a flowchart illustrating beam forming by the receive beam former 104.

First, in Step S101, the transmitter 1031 performs transmission processing (a transmission event) of supplying a transmission signal causing transmission of an ultrasound beam to each transmission transducer element of the transmission aperture Tx.

In Step S102, the receiver 1040 generates receive signal sequences based on electric signals yielded through the reception of reflected ultrasound by the probe 101, and outputs the receive signal sequences to be stored in the data storage 107. Then, a determination is made of whether or not all transducer elements 101a of the probe 101 have performed ultrasound transmission (S103). When one or more of the transducer elements 101a have not yet performed ultrasound transmission, processing returns to Step S101, which results in another transmission event being executed by shifting the transmission aperture Tx in the transducer element array direction by the width of a single transducer element. Meanwhile, when all of the transducer elements 101a have performed ultrasound transmission, processing proceeds to Step S210.

In Step S210, the target line group setter 1042 sets a target line group Bx for a processing-target transmission event based on information indicating the position of the transmission aperture Tx for the processing-target transmission event. In the initial loop of processing, the target line group setter 1042 sets a target line group Bx for the initial transmission event, which can be calculated from the transmission aperture Tx for the initial transmission event.

Subsequently, processing proceeds to measurement-point dependent beam forming (Step S220 (including Steps S221 through S228)). In Step S220, first, coordinate values i and j indicating a position of a measurement point Pij of the target line group Bx for the processing-target transmission event are initialized (set to the respective minimum possible values in the target line group Bx) (Steps S221 and S222). Then, the receive aperture setter 1043 sets a receive aperture Rx for the current measurement point so that the center of the receive aperture Rx corresponds to a transducer element Xk that is spatially closest to the current measurement point Pij (Step S223).

Subsequently, an acoustic line signal is generated for the current measurement point Pij (Step S224).

Figure 12:
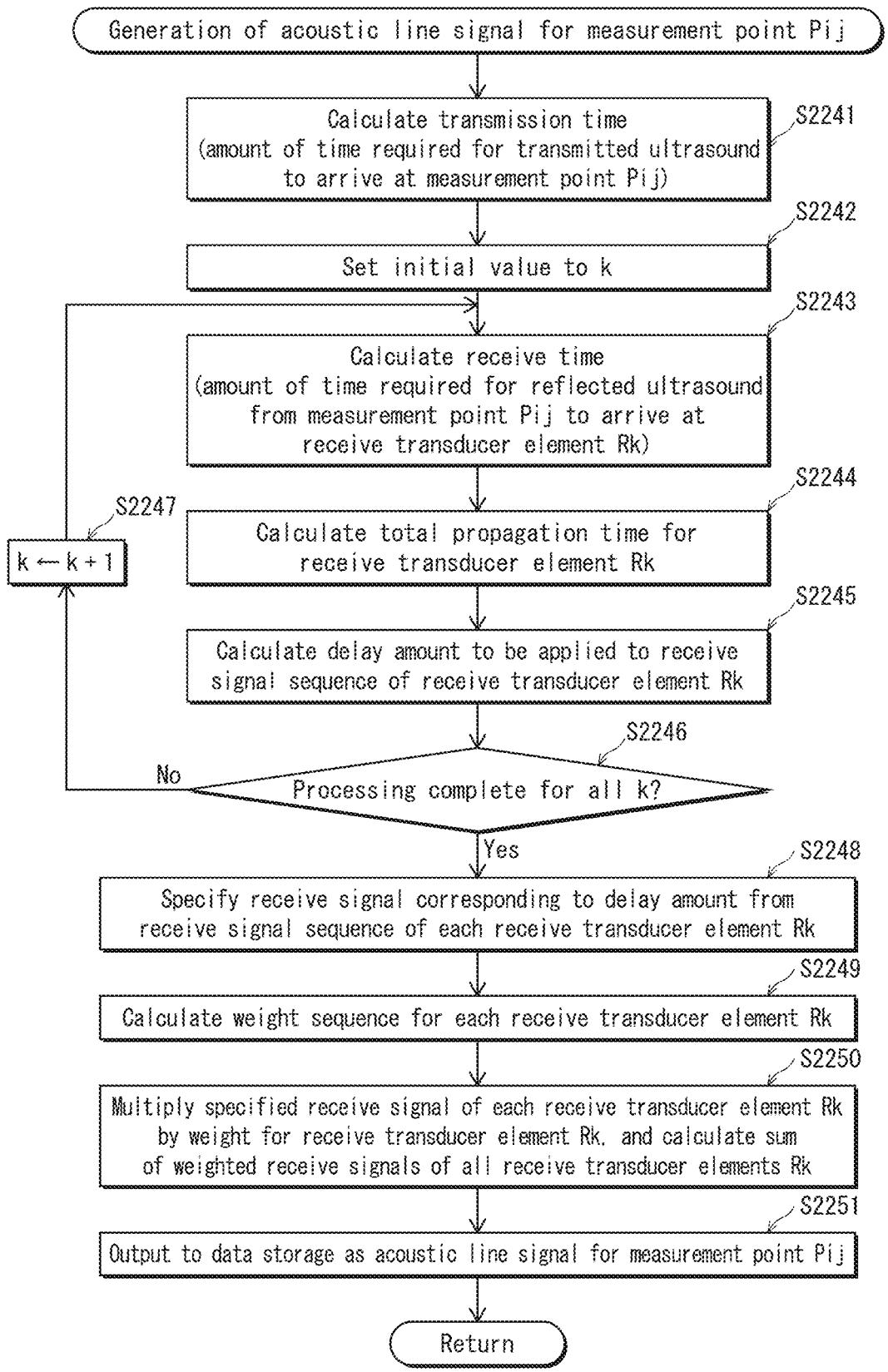
FIG. 12 is a flowchart illustrating operations of the receive beam former 104 pertaining to the embodiment for generating an acoustic line signal for a measurement point Pij.
Figure 13:
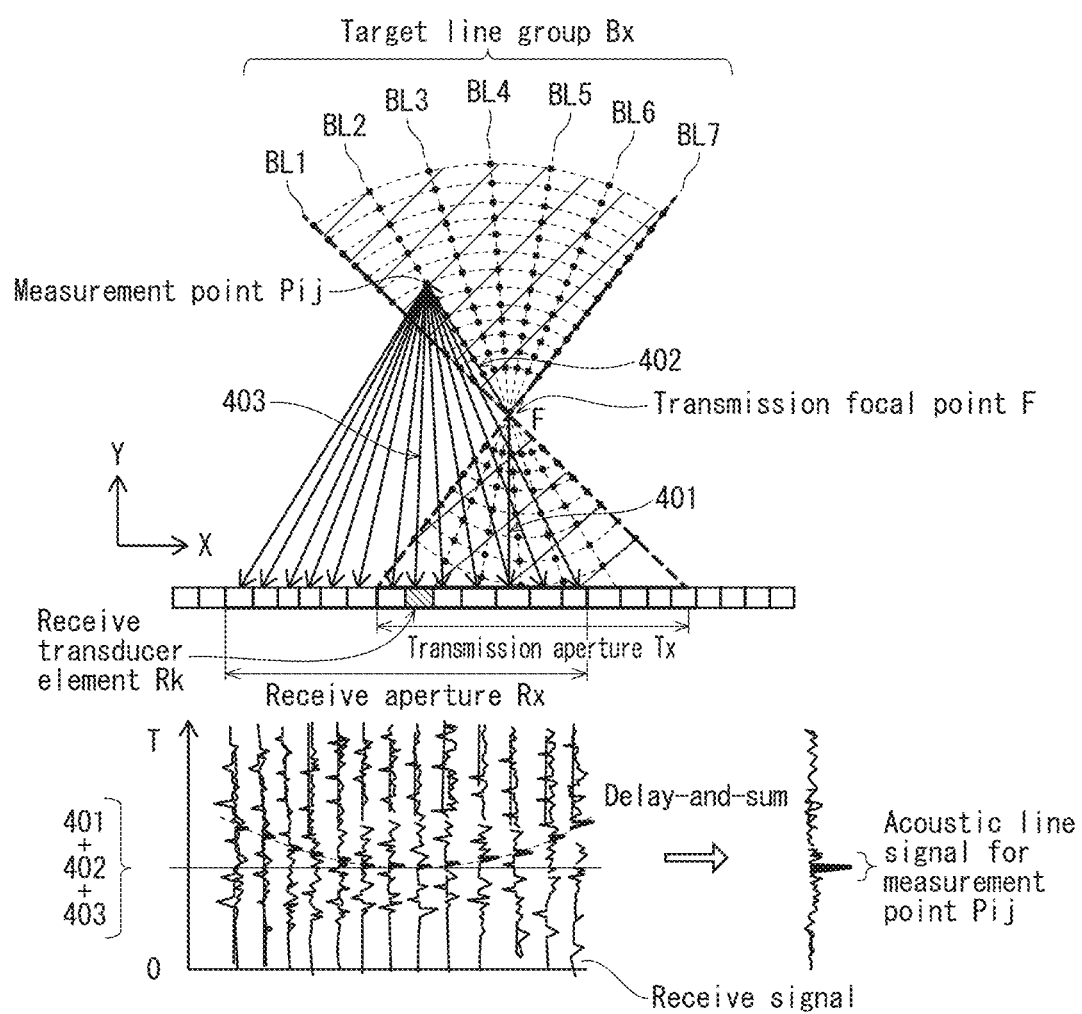
FIG. 13 is a schematic for explaining the operations of the receive beam former 104 pertaining to the embodiment for generating an acoustic line signal for a measurement point Pij.

The following describes the operations in Step S224 for generating an acoustic line signal for the current measurement point Pij. FIG. 12 is a flowchart illustrating the operations of the receive beam former 104 for generating the acoustic line signal for the current measurement point Pij. FIG. 13 is a schematic for explaining the operations of the receive beam former 104 for generating the acoustic line signal for the current measurement point Pij.

First, in Step S2241, the transmission time calculator 1044 calculates, for the current measurement point Pij, a transmission time required for transmitted ultrasound to arrive at the current measurement point Pij. As already described above, the current measurement point Pij is a measurement point of the target line group Bx for the processing-target transmission event. Here, (i) when the current measurement point Pij is located at the transmission focal depth or deeper than the transmission focal depth, the transmission time for the current measurement point Pij is calculated by dividing, by ultrasound velocity cs, the geometrically-calculable length of a path (combination of paths 401 and 402) starting at a transmission transducer element in the transmission aperture Tx and reaching the current measurement point Pij via the transmission focal point F. Meanwhile, (ii) when the current measurement point Pij is located shallower than the transmission focal depth, the transmission time for the current measurement point is calculated by dividing, by the ultrasound velocity cs, a value (401-402) obtained by subtracting the geometrically-calculable length of the path from the transmission focal point F to the current measurement point Pij from the geometrically-calculable length of the path from a transmission transducer element in the transmission aperture Tx to the transmission focal point F.

Subsequently, value k, which indicates the position of a target receive transducer element Rk of the receive aperture Rx, is initialized (set to the minimum possible value in the receive aperture Rx) (Step S2242). Then, the receive time for the target receive transducer element Rk is calculated (Step S2243). The receive time is the time required for transmitted ultrasound to arrive at the target receive transducer element Rk after being reflected at the current measurement point Pij. The receive time for the target receive transducer element Rk can be calculated by dividing, by the ultrasound velocity cs, the geometrically-calculable length of the path 403 from the current measurement point Pij to the target receive transducer element Rk. Further, from a sum of the transmission time and the receive time for the target receive transducer element Rk, the total propagation time required for ultrasound transmitted from the transmission aperture Tx to arrive at the target receive transducer element Rk after being reflected at the current measurement point Pij is calculated (Step S2244). Further, based on the difference in total propagation time between different receive transducer elements Rk composing the receive aperture Rx, the delay amount for the target receive transducer element Rk is calculated (Step S2245).

Subsequently, a determination is performed of whether or not a delay amount has been calculated for every receive transducer element Rk composing the receive aperture Rx (Step S2246). When a delay amount has not yet been calculated for one or more of the receive transducer elements Rk, the value k is incremented (Step S2247), and a delay amount for another receive transducer element Rk is calculated (Step S2243). Meanwhile, when a delay amount has been calculated for every receive transducer element Rk composing the receive aperture Rx, processing proceeds to Step S2248. Note that at this point, a delay amount for the current measurement point Pij has already been calculated for each receive transducer element Rk of the receive aperture Rx. The delay amount for a given receive transducer element Rk indicates delay with which reflected ultrasound from the current measurement point Pij arrives at the receive transducer element Rk.

In Step S2248, the delay processor 1047, for each receive transducer element Rk, specifies a receive signal based on reflected ultrasound from the current measurement point Pij. Here, the delay processor 1047 specifies, from a receive signal sequence corresponding to each receive transducer element Rk, a receive signal corresponding to a time point after subtraction of the delay amount for the receive transducer element Rk.

Subsequently, the weight calculator 1048 calculates a weight sequence for the receive transducer elements Rk of the current receive aperture Rx, so that the maximum weight is set with respect to the receive transducer element located at the center position of the receive aperture Rx in the transducer element array direction (S2249). Then, the sum calculator 1049 generates an acoustic line signal for the current measurement point Pij by multiplying the specified receive signal for each receive transducer element Rk by a weight corresponding to the receive transducer element Rk, and summing the weighted receive signals for the different receive transducer elements Rk (Step S2250). Following this, the sum calculator 1049 outputs the acoustic line signal for the current measurement point Pij to the data storage 107 to be stored in the data storage 107 (Step S2251).

Referring to FIG. 11 once again, subsequently, an acoustic line signal is generated for each measurement point Pij (each illustrated in FIG. 13 as a black dot) of the target line group Bx for the processing-target transmission event, by repeating Steps S223, S224 while incrementing the coordinate values i and j (Steps S225, S227). Subsequently, a determination is performed of whether or not an acoustic line signal has been generated for every measurement point Pij of the target line group Bx. When an acoustic line signal has not yet been generated for every measurement point Pij of the target line group Bx, the coordinate values i and j are incremented, yielding an acoustic line signal for another measurement point Pij (Step S224). Meanwhile, when an acoustic line signal has already been generated for every measurement point Pij of the target line group Bx, processing proceeds to Step S230. At this point, an acoustic line signal has already been generated for each measurement point P of the target line group Bx corresponding to the processing-target transmission event, and the acoustic line signals have been output to and stored to the data storage 107. In other words, a sub-frame acoustic line signal for the processing-target transmission event has been generated, and output to and stored to the data storage 107.

Subsequently, a determination is performed of whether or not a sub-frame acoustic line signal has been generated for each transmission event having been performed (Step S230). When sub-frame acoustic line signals have not yet been generated for one or more transmission events, processing proceeds to Step S210, where the coordinate values i and j are initialized (set to the respective minimum possible values in the target line group Bx for the subsequent transmission event, which can be calculated from the transmission aperture Tx for the subsequent transmission event) (Steps S221 and S222), and then setting of a receive aperture Rx is performed (Step S223). Meanwhile, when sub-frame acoustic line signals have been generated for every transmission event having been performed, processing proceeds to Step S301.

In Step S301, the adder 11401 reads out the sub-frame acoustic line signals stored in the data storage 107, and combines the sub-frame acoustic line signals based on positions of the measurement points Pij. Thus, a combined acoustic line signal is generated for each measurement point Pij, and accordingly, a frame acoustic line signal is generated. Subsequently, the amplifier 11402 multiples each combined acoustic line signal by a corresponding amplification factor that is determined based on the number of acoustic line signals, included in the sub-frame acoustic line signals, that have been combined to yield the combined acoustic line signal (Step S302). Further, the amplifier 11402 outputs the amplified frame acoustic line signal to the ultrasound image generator 105 and the data storage 107 (Step S303), and processing is terminated.

<Effect of Receive Beam Forming>

The following describes the effect of the present embodiment by comparing receive beam forming that is an implementation example and three types of receive beam forming that are comparative examples in terms of achieved ultrasound image quality.

(1) Receive Beam Forming

In the implementation example, the target line group Bx is composed of multiple target lines. Further, one target line is located on the center axis Txo of the transmission aperture, and two target lines are located on the outer boundaries of the ultrasound main irradiation area Ax. Further, every pair of adjacent ones of the target lines forms the same angle (predetermined angle d) therebetween.

Figure 14A:
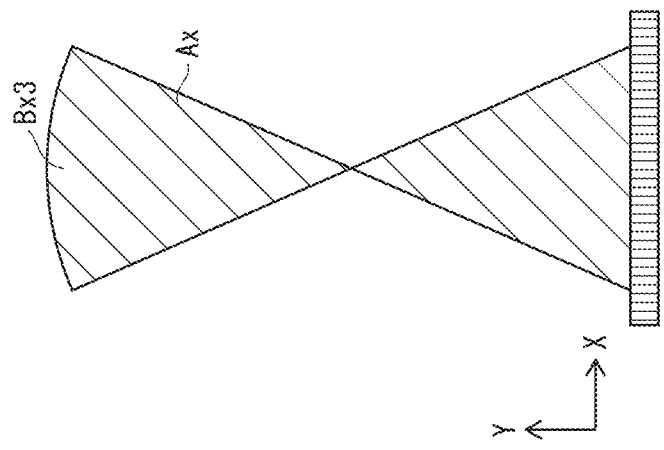
FIGS. 14A through 14C are schematics illustrating shapes of target areas of comparative examples 1 through 3.

Meanwhile, in comparative example 1 illustrated in FIG. 14A, a target area Bx1 is used that is composed of a straight line that passes through the focal point F and that is perpendicular to the transducer element array direction. This means that the receive beam forming of comparative example 1 does not use the synthetic aperture method. Note that in comparative example 1, the calculation of transmission time may be performed using only measurement point depth. This change in calculation method has no influence on the resulting ultrasound images. This is because, for measurement points along the target area Bx1 of comparative example 1, a transmission time calculated according to the present embodiment and a transmission time calculated according to the conventional technique of using only measurement point depth are exactly equal. Further, the number of measurement points along the target area Bx1 equals the number of measurement points along one target line in the implementation example. Thus, the delay-and-summing computation amount in comparative example 1 is greater than 0.1 times and smaller than 0.4 times that in the implementation example.

Figure 14B:
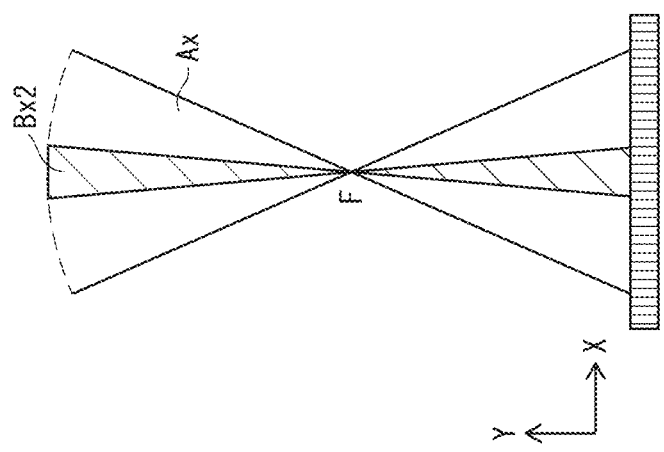

In comparative example 2 illustrated in FIG. 14B, a target area Bx2 is used which includes the focal point F and whose width in the transducer element array direction (x direction) is smaller than the width of the ultrasound main irradiation area Ax in the transducer element array direction (x direction). Note that the target area Bx2 is such that: (i) measurement point density of target area Bx2 is equal to measurement point density of target line group Bx along target lines; and (ii) the number of measurement points Pij included in target area Bx2 is equal to the number of measurement points Pij included in target line group Bx. Thus, the ratio between the angular range of target area Bx2 and the angular range of ultrasound main irradiation area Ax is equal to the ratio between measurement point density of target line group Bx transverse to target lines and measurement point density of the target line group Bx along target lines. Since the number of measurement points in comparative example 2 equals the number of measurement points in the implementation example, the delay-and-summing computation amount in comparative example 2 is exactly the same as that in the implementation example.

Figure 14C:
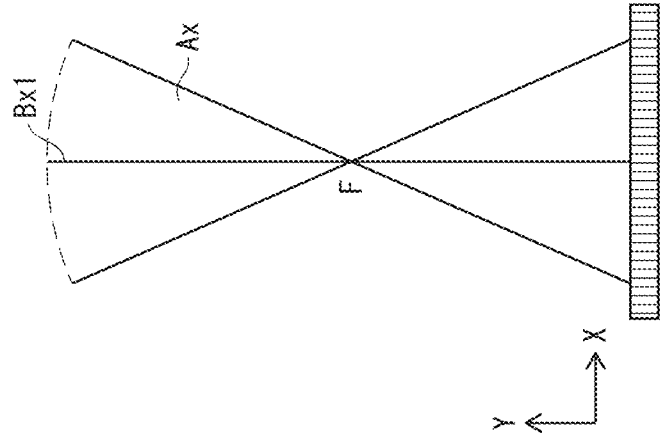

In comparative example 3 illustrated in FIG. 14C, a target area Bx3 is used that equals the entirety of the ultrasound main irradiation area Ax. Note that measurement point density of target area Bx3 is equal to measurement point density of target area Bx2 and measurement point density of target line group Bx along target lines. Thus, the ratio between the number of measurement points in target line group Bx (or target area Bx2) and the number of measurement points in target area Bx3 is equal to the ratio between the angular range of target area Bx2 and the angular range of ultrasound main irradiation area Ax, and is also equal to the ratio between measurement point density of target line group Bx transverse to target lines and measurement point density of target line group Bx along target lines. Note that the number of measurement points in target area Bx3 equals the number of measurement points when the number of measurement points in the target line group Bx is increased so that measurement point density transverse to target lines equals measurement point density along target lines. Due to this, the delay-and-summing computation amount in comparative example 3 is at least approximately three times that in the implementation example.

(2) Ultrasound Image Quality

FIGS. 15A trough 15D show ultrasound images (B-mode tomographic images) acquired by image-capturing the same imaging phantom by using the receive beam forming method of the implementation example and the receive beam forming methods of comparative examples 1 through 3. Specifically, FIG. 15C corresponds to the implementation example, and FIGS. 15A, 15B, and 15D respectively correspond to comparative examples 1, 2, and 3. Note that in each of these drawings, the ultrasound beam travel direction is the direction from top to bottom in the drawing.

As illustrated in FIG. 15A, with comparative example 1, (i) the greater the distance from the focal depth (depth of the circular bright spot), the greater the bleeding of bright spots, which should have circular shapes, in the transducer element array direction, and (ii) the greater the depth, the greater the amount of noise and the more unclear the image. These problems are considered to have occurred due to ultrasound beams becoming more out of focus, transmitted ultrasound amplitude decreasing, and phase lag increasing, as distance from the focal point F increases Meanwhile, as illustrated in FIG. 15D, with comparative example 3, bleeding of bright spots is seldom observed (i.e., the bright spots have circular shapes) and image clarity is high at all areas, despite the image being dark at the bottommost area of the image. This is believed to be due to virtual beam forming of combining sub-frame acoustic line signals acquired from multiple transmission events resulting in acoustic line signals supplementing one another to cancel out noise components, and thereby achieving an improvement in acoustic line signal resolution and S/N ratio.

Further, the following results were achieved with comparative example 2 and the implementation example. FIG. 15B shows an ultrasound image pertaining to comparative example 2, and FIG. 15C shows an ultrasound image pertaining to the implementation example. As illustrated in FIG. 15C, with the implementation example, while noise at deep areas has higher intensity than with comparative example 3, bleeding of bright spots is seldom observed (i.e., the bright spots have circular shapes), and image clarity is high at all areas. On the other hand, as illustrated in FIG. 15B, with comparative example 2, while noise at deep areas has lower intensity than with implementation example 1, (i) the greater the distance from the focal depth, the greater the bleeding of bright spots, which should have circular shapes, in the transducer element array direction, and (ii) the greater the depth, the greater the amount of noise and the more unclear the image. That is, while the number of measurement points and thus the delay-and-summing computation amount are equal between the implementation example and comparative example 2, image quality achieved with comparative example 2 is prominently lower than that achieved with comparative example 3, whereas image quality achieved with the implementation example is not prominently lower than that acquired with comparative example 3.

(3) Analysis of Results

The implementation example and comparative example 2 achieve a same level of reduction in computation amount from comparative example 3. However, there is a great difference in achieved acoustic line signal quality between implementation example and comparative example 2, which is considered to have occurred due to the following reasons. Each of FIGS. 16A through 16D corresponds to one of the implementation example, comparative example 1, comparative example 2, and comparative example 3, and is a schematic illustrating, for one measurement point Pij whose combined acoustic line signal is included in a frame acoustic line signal, the target lines, of the target line groups corresponding to the different transmission events, on which the measurement point Pij is located.

Figures 16A, 16B, 16C, 16D:
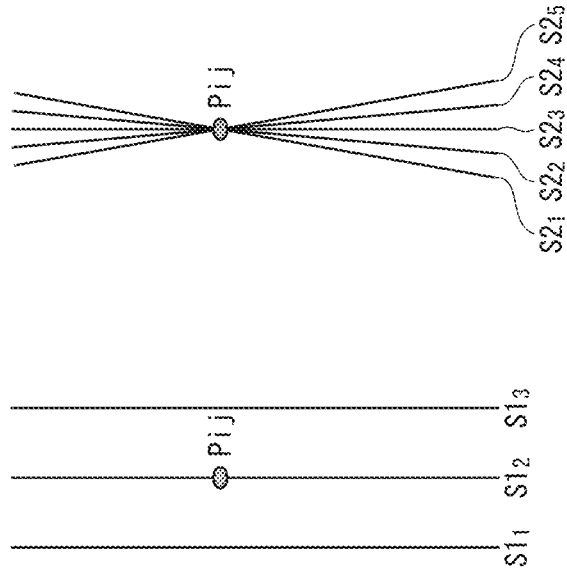
FIGS. 16A through 16D are schematics illustrating a relation between ultrasound beam travel directions and a measurement point, in the implementation example and comparative examples 1 through 3.

As illustrated in FIG. 16A, in comparative example 1, the combined acoustic line signal for the measurement point Pij in the frame acoustic line signal is generated by using only one acoustic line signal acquired from a transmission event for which the straight line $S1_2$ is used as a target line. In this case, sub-frame acoustic line signals acquired from transmission events for which the other straight lines $S1_1$ and $S1_3$ are used as target lines cannot be used for generating the combined acoustic line signal for the measurement point Pij, due to the measurement point Pij not being located on these straight lines. Due to this, the frame acoustic line signal is generated by merely aligning, in the transducer element array direction, sub-frame acoustic line signals whose spatial coordinates do not overlap. That is, virtual beam forming of combining sub-frame acoustic line signals acquired from multiple transmission events is not performed in this case. Accordingly, the distance resolution and the S/N ratio of the frame acoustic line signal are equal to the distance resolution and the S/N ratio of individual sub-frame acoustic line signals. Further, a decrease in acoustic line signal quality, brought about by ultrasound beams becoming out of focus and signal intensity decreasing, becomes more prominent as the distance from the focal depth increases.

Meanwhile, as illustrated in FIG. 16C, in comparative example 3, the combined acoustic line signal for the measurement point Pij is generated by using a plurality of acoustic line signals corresponding to different ultrasound beam travel directions. For example, the combined acoustic line signal for the measurement point Pij is generated by using an acoustic line signal for the measurement point Pij acquired from a transmission event whose target area includes straight line $S3_1$ passing through measurement point Pij as a target line, an acoustic line signal for the measurement point Pij acquired from a transmission event whose target area includes straight line $S3_2$ passing through measurement point Pij as a target line, . . . , and an acoustic line signal for the measurement point Pij acquired from a transmission event whose target area includes straight line $S3_n$ passing through measurement point Pij as a target line. Due to this, acoustic line signals corresponding to ultrasound beams with different travel directions are combined, and thus the combined acoustic line signal for measurement point Pij has high spatial resolution and high S/N ratio.

The following description is provided supposing that the overlap count for the measurement point Pij is five in both comparative example 2 and the implementation example. In this case, in both comparative example 2 and the implementation example, the combined acoustic line signal for the measurement point Pij is generated by combining five acoustic line signals acquired from different transmission events. However, comparative example 2 and implementation example differ in terms of ultrasound beam travel directions of the five transmission events. As illustrated in FIG. 16B, in comparative example 2, the combined acoustic line signal for the measurement point Pij is generated by using an acoustic line signal for the measurement point Pij acquired from a transmission event whose target area includes straight line $S2_1$ passing through measurement point Pij as a target line, an acoustic line signal for the measurement point Pij acquired from a transmission event whose target area includes straight line $S2_2$ passing through measurement point Pij as a target line, . . . , and an acoustic line signal for the measurement point Pij acquired from a transmission event whose target area includes straight line $S2_5$ passing through measurement point Pij as a target line. Meanwhile, as illustrated in FIG. 16D, in the implementation example, the combined acoustic line signal for the measurement point Pij is generated by using an acoustic line signal for the measurement point Pij acquired from a transmission event whose target area includes straight line $S4_1$ passing through measurement point Pij as a target line, an acoustic line signal for the measurement point Pij acquired from a transmission event whose target area includes straight line $S4_p$ passing through measurement point Pij as a target line, an acoustic line signal for the measurement point Pij acquired from a transmission event whose target area includes straight line $S4_m$ passing through measurement point Pij as a target line, an acoustic line signal for the measurement point Pij acquired from a transmission event whose target area includes straight line $S4_q$ passing through measurement point Pij as a target line, and an acoustic line signal for the measurement point Pij acquired from a transmission event whose target area includes straight line $S4_n$ passing through measurement point Pij as a target line.

In comparative example 2, the straight lines $S2_1$ through $S2_5$ are densely arranged, and thus, the angle between the straight lines $S2_1$ and $S2_5$ is smaller than the angle between the straight lines $S3_1$ and $S3_n$ in comparative example 3. Meanwhile, in the implementation example, the angle between the straight lines $S4_1$ and $S4_n$ is equal to the angle between the straight lines $S3_1$ and $S3_n$ in comparative example 3. The two following effects can be considered as reasons why acoustic line signal spatial resolution and S/N ratio increase by performing virtual beam forming of combining sub-frame acoustic line signals acquired form multiple transmission events. (i) Since distance resolution and directional resolution vary depending upon ultrasound beam travel direction, spatial resolution and S/N ratio improve due to complementation occurring by combining acoustic line signals acquired by using ultrasound beams with different travel directions. (ii) Acoustic line signals acquired by using ultrasound beams with different travel directions correspond to different positional relationships between the measurement point, the receive aperture for the measurement point, and focal point F, and thus differ in terms of pattern of noise influenced by the surrounding of the measurement point. By combining acoustic line signals acquired by using ultrasound beams with different travel directions, noise is cancelled out and an improvement in S/N ratio can be achieved. Accordingly, in order to strengthen effects (i) and (ii), it is preferable that the angular difference be great between the target lines from which the acoustic line signals to be combined are generated.

Based on the above, the following assumptions can be made. In connection with effect (i), the range of ultrasound beam travel directions is smaller with comparative example 2 than with the implementation example and comparative example 3, and the complementation effect achieved by combining acoustic line signals corresponding to different ultrasound beam travel directions is smaller with comparative example 2 than with the implementation example and comparative example 3. Further, in connection with effect (ii), due to the range of variation of the positional relationships between the measurement point, the receive aperture for the measurement point, and focal point F being smaller with comparative example 2 than with the implementation example and comparative example 3, different transmission events produced artifacts that were oriented in the direction perpendicular to the ultrasound beam travel directions and that were spatially close to one another. Due to this, the artifacts remained without being cancelled out to form an artifact extending in the transducer element array direction.

Meanwhile, the following assumption can be made regarding the implementation example. That is, in connection with effect (i), although the overlap count is smaller with the implementation example than with comparative example 3, the range of ultrasound beam travel directions is similarly wide with the implementation example and with comparative example 3, and the complementation effect achieved by combining acoustic line signals is sufficient with the implementation example. Further, in connection with effect (ii), due to the range of variation of the positional relationships between the measurement point, the receive aperture for the measurement point, and focal point F being similar between the implementation example and comparative example 3, the implementation example achieves an improvement in S/N ratio. That is, an assumption can be made that the effect achieved by virtual beam forming of combining acoustic line signals acquired from different transmission events is not influenced much by the overlap count, and rather, is influenced much by factors such as the range of ultrasound beam travel directions and the range of variation of the positional relationships between the measurement point, the receive aperture for the measurement point, and focal point F.

It is considered that the implementation example suppressed degradation in acoustic line signal resolution and acoustic line signal S/N ratio while rendering computation amount considerably small compared to comparative example 3 due to the above-described reasons.

In the above, description is provided that the computation amount with the implementation example is no greater than approximately one third of the computation amount with comparative example 3. However, it is preferable that the number of measurement points and computation amount pertaining to the present embodiment be approximately 20% those pertaining to comparative example 3, or smaller. By making this configuration, an approximately 80% reduction in computation amount can be achieved. Consequently, it becomes possible to realize an ultrasound diagnostic device with low cost by using a processor with ordinary computation capability and to allocate processor computation capability to expansion of ROIs and improvement of frame rate.

<Conclusion>

As described above, the ultrasound diagnostic device 100 pertaining to the present embodiment, according to the synthetic aperture method, synthesizes acoustic line signals for the same measurement point that are generated from different transmission events. This achieves the effect of performing, for multiple transmission events, virtual transmission focusing even for measurement points that are located in depths other than that of the transmission focal point F. This improves spatial resolution and S/N ratio.

In addition, in the ultrasound diagnostic apparatus 100, a target area, which is an area from which a sub-frame acoustic line signal is generated, is set to be composed of multiple target lines passing through the focal point F or the focal area. Due to this, the number of measurement points can be reduced without directly reducing the size of the area in which measurement points exist and without reducing measurement point density in the depth direction. Consequently, a great reduction in delay-and-summing computation amount can be achieved while maintaining high spatial resolution and signal S/N ratio in the depth direction. In addition, there is also no substantial decrease in spatial resolution and signal S/N ratio in the transducer element array direction. This is because the area in which measurement points exist is not reduced in size and thus the possible directional ranges of ultrasound paths between transducer elements and measurement points are not narrowed down, whereby the effects of combining different acoustic line signals acquired from the same measurement point (i.e., improvement in spatial resolution and signal S/N ratio) are achieved. Accordingly, the present embodiment considerably reduces computation amount compared to ultrasound diagnostic devices using conventional synthetic aperture methods while suppressing degradation of acoustic line signal quality, and contributes to a reduction of processor cost.

Further, in the ultrasound diagnostic device 100, the receive aperture setter 1043 selects, as transducer elements composing the receive aperture Rx for each measurement point P, transducer elements forming an array whose center position in the transducer element array direction matches a transducer element that is spatially closest to the measurement point P. Accordingly, the ultrasound diagnostic device 100 performs receive beam forming by using a receive aperture that is not dependent upon ultrasound transmission events but is dependent upon the position of the measurement point P, and that is symmetric with respect to the measurement point P. Due to this, the receive aperture Rx for a given measurement point P does not change (i.e., the same receive aperture Rx is used for the same measurement point P) between different transmission events, between which the transmission focal point F is shifted in the transducer element array direction. Thus, delay-and-sum processing for the same measurement point P is always performed by using the same receive aperture Rx. In addition, in the ultrasound diagnostic device 100, a weight sequence is set so that the closer a receive transducer element is to the measurement point P, the greater the weight applied to the receive transducer element. Due to this, even taking into account the fact that ultrasound decay increases as propagation distance increases, ultrasound reflected from the measurement point P can be used with high efficiency. Accordingly, the ultrasound diagnostic device 100 achieves both high local spatial resolution and high S/N ratio.

<<Modification 1>>

The receive aperture setter 1043 in the ultrasound diagnostic device 100 pertaining to the embodiment sets, for each measurement point P, the receive aperture Rx so that the center position of the receive aperture Rx in the transducer element array direction corresponds to a transducer element that is spatially closest to the measurement point P. However, the configuration of the receive aperture Rx may be changed as necessary, as long as acoustic line signals for all measurement points Pij of the target line group Bx can be generated by calculating total propagation times and performing delaying based on total propagation paths. As already discussed above, a total propagation time for a given receive transducer element Rk is the time required for ultrasound transmitted from the transmission aperture Tx to reach the receive transducer element Rk after passing through the transmission focal point F and being reflected at the measurement point P.

Modification 1 provides an ultrasound diagnostic device differing from the ultrasound diagnostic device 100 pertaining to the embodiment for including a receive aperture setter (a Tx receive aperture setter) that sets, for each transmission event, the receive aperture Rx so that the center position of the receive aperture Rx corresponds to the center position of the transmission aperture Tx for the transmission event. That is, the receive aperture Rx in modification 1 can be referred to as a transmission-dependent receive aperture. Other than the Tx receive aperture setter, the components of the ultrasound diagnostic device pertaining to modification 1 have the same structures and configurations as the corresponding components in the ultrasound diagnostic device 100 described in the embodiment. Thus, description of such similar components is not provided in the following.

Figure 17:
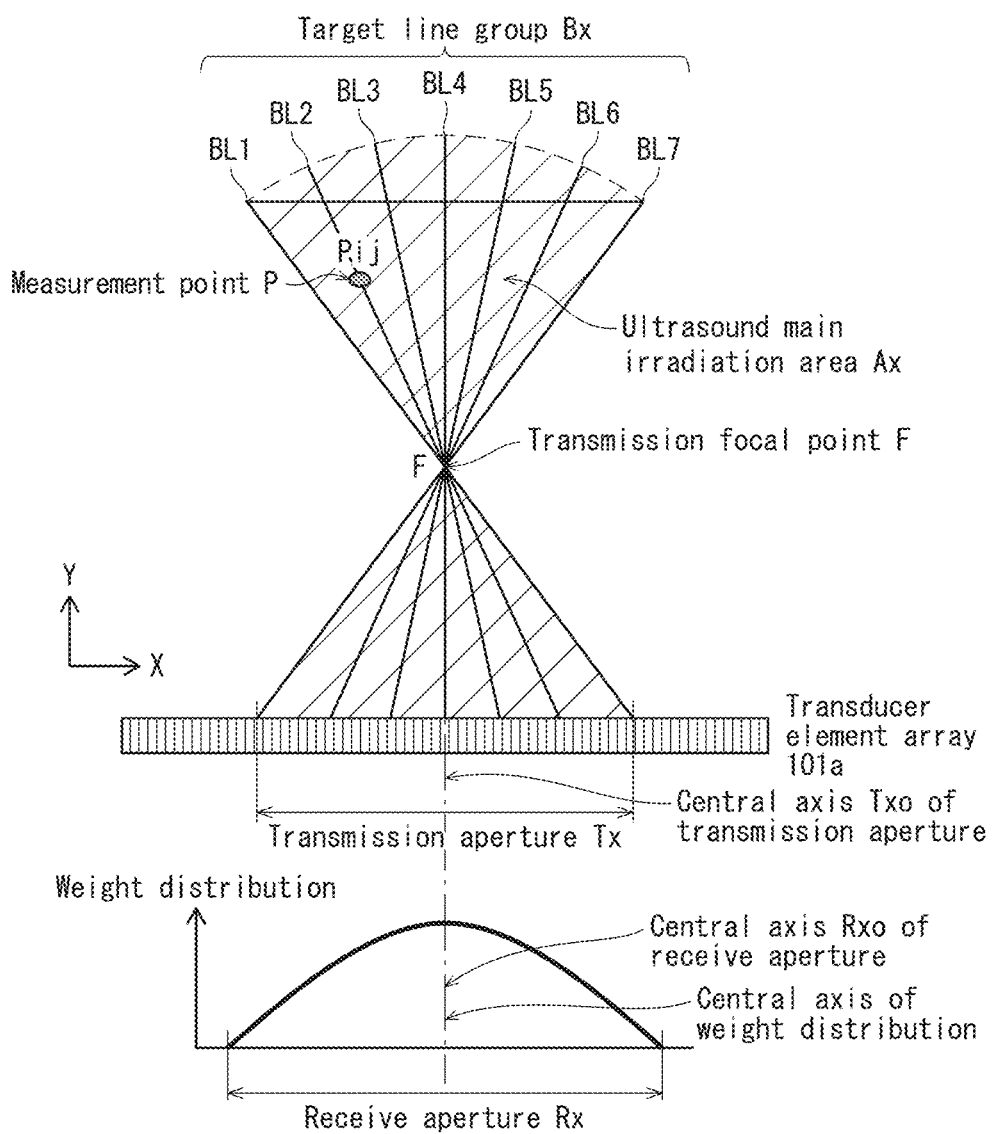
FIG. 17 is a schematic illustrating the relationship between a transmission aperture Tx and a receive aperture Rx set by a Tx receive aperture setter pertaining to modification 1.

FIG. 17 is a schematic illustrating the relationship between a transmission aperture Tx and a receive aperture Rx set by the Tx receive aperture setter. In modification 1, the Tx receive aperture setter sets, for each transmission event, a receive aperture Rx so that the center position of the receive aperture Rx in the transmission element array direction corresponds to the center position of the transmission aperture Tx for the transmission event. Thus, the position of an axis Rxo passing through the center position of the receive aperture Rx corresponds to the position of an axis Txo passing through the center position of the transmission aperture Tx. Further, the receive aperture Rx is symmetric about the transmission focal point F (i.e., has the same number of apertures at both sides of the center position thereof in the transmission element array direction). As such, as the transmission aperture Tx shifts in the transducer element array direction from one transmission event to another, the receive aperture Rx also shifts in the transducer element array direction, following the transmission aperture Tx.

In addition, a weight sequence (so-called reception apodization weight) for the receive transducer elements Rk is calculated, so that the maximum weight is set with respect to the receive transducer element Rk located along the center axis Rxo of the receive aperture Rx and the center axis Txo of the transmission aperture Tx. The weight sequence indicates weights distributed symmetrically with respect to the transducer element Xk. As the shape of distribution of the weights indicated by the weight sequence, any shape is applicable, including but not limited to a hamming window, a hanning window, and a rectangular window.

<Operations>

Figure 18:
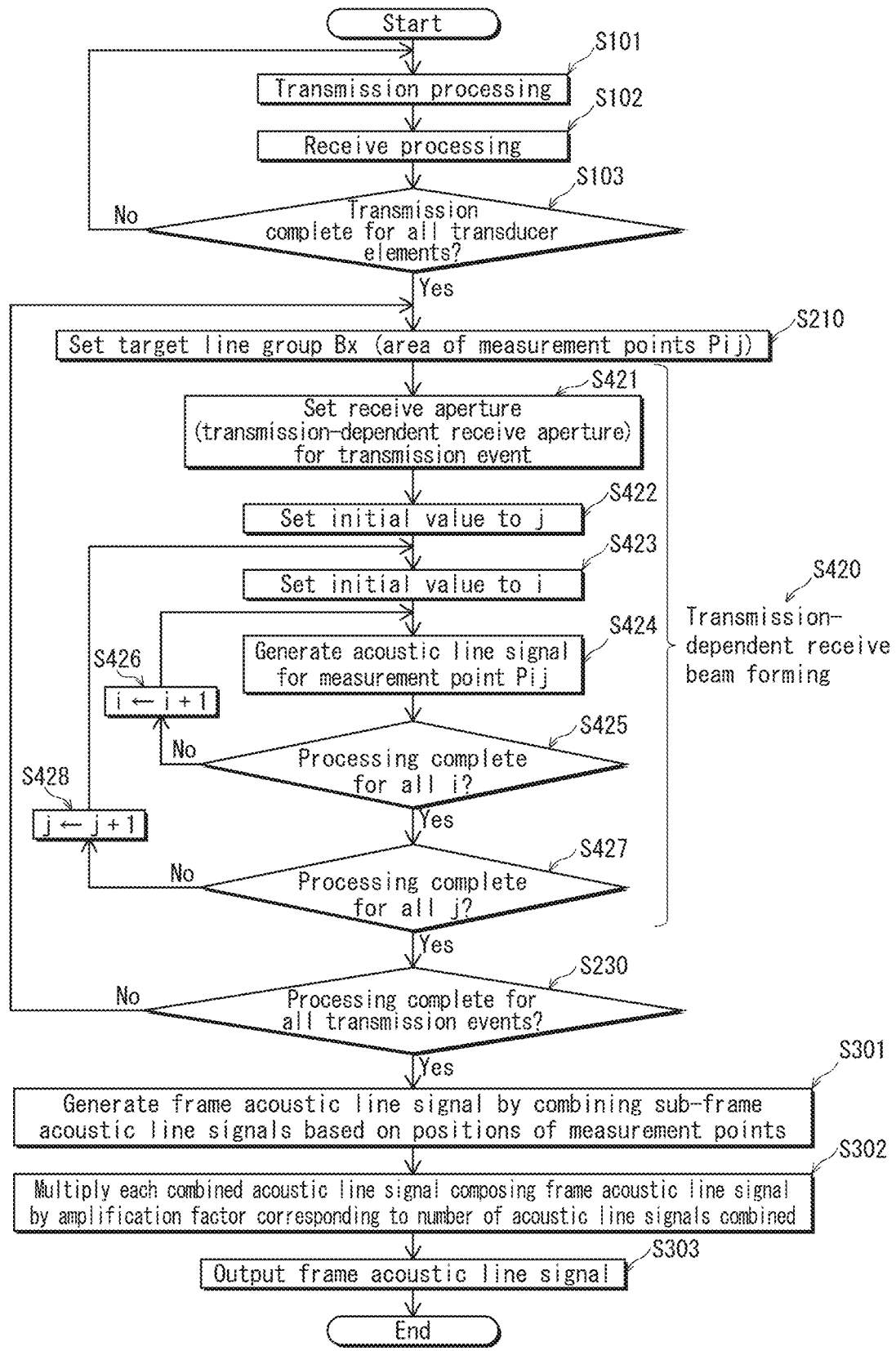
FIG. 18 is a flowchart illustrating beam forming by a receive beam former of an ultrasound diagnostic device pertaining to modification 1.

FIG. 18 is a flowchart illustrating beam forming by a receive beam former of the ultrasound diagnostic device pertaining to modification 1. The flowchart in FIG. 18 differs from the flowchart in FIG. 11 for transmission-dependent dependent beam forming (Step S420 (including Steps S421 through S428)) being performed in place of measurement point-dependent beam forming (Step S220 (including Steps S221 through S228)). Meanwhile, the processing in steps other than Step S420 in the flowchart in FIG. 15 is similar to the processing in the corresponding steps in the flowchart in FIG. 11. Thus, description of such similar processing is not provided in the following.

In Step S420, first, the Tx receive aperture setter sets a receive aperture Rx for a transmission event by selecting receive transducer elements Rk composing a receive transducer element array whose center position matches the center position of the transducer element array composing the transmission aperture Tx for the corresponding transmission event, in Step S421.

Figure 19:
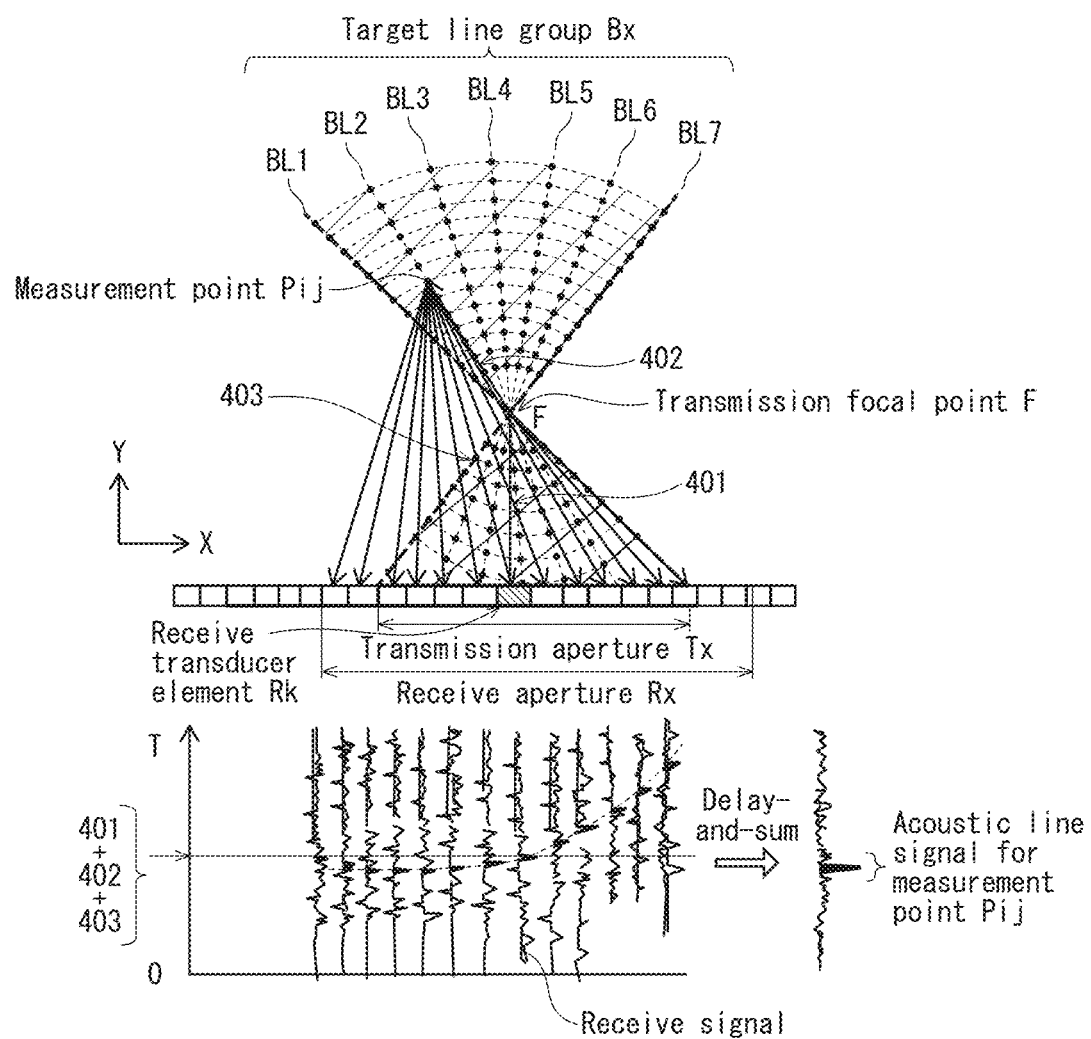
FIG. 19 is a schematic for explaining the operations of the receive beam former pertaining to modification 1 for generating an acoustic line signal for a measurement point Pij.

Subsequently, coordinate values i and j indicating a position of a measurement point Pij of the target line group Bx for the processing-target transmission event are initialized (set to the respective minimum possible values in the target line group Bx set in Step S210) (Steps S422 and S423). Subsequently, an acoustic line signal is generated for the current measurement point Pij (Step S424). FIG. 19 is a schematic for explaining the operations of the receive beam former pertaining to modification 1 for generating the acoustic line signal for the current measurement point Pij. FIG. 19 differs from FIG. 13 referred to in the embodiment in terms of the positional relationship between the transmission aperture Tx and the receive aperture Rx. The processing in Step S424 is similar to that in Step S224 of FIG. 11 (i.e., Steps S2241 through S2251 in FIG. 12).

An acoustic line signal is generated for each measurement point Pij (each illustrated in FIG. 19 as a black dot) of the target line group Bx by repeating Step S424 while incrementing the coordinate values i and j. Subsequently, a determination is performed of whether an acoustic line signal has not yet been generated for one or more of the measurement points Pij of the target line group Bx (Steps S425, S427). When an acoustic line signal has not yet been generated for every measurement point Pij of the target line group Bx, the coordinate values i and j are incremented (Steps S426 and S428), yielding an acoustic line signal for another measurement point Pij (Step S424). Meanwhile, when an acoustic line signal has already been generated for every measurement point Pij of the target line group Bx, processing proceeds to Step S230. At this point, an acoustic line signal has already been generated for each measurement point Pij of the target line group Bx for the processing-target transmission event, and the acoustic line signals have been output to and stored to the data storage 107.

<Effects>

The ultrasound diagnostic device pertaining to modification 1, which has been described up to this point, achieves the effects described in the embodiment, excluding the effect related to setting a measurement point-dependent receive aperture. In place of the effect related to setting a measurement point-dependent receive aperture, the ultrasound diagnostic device pertaining to modification 1 achieves the following effect. In modification 1, for each transmission event, the receive aperture Rx is set by selecting receive transducer elements forming a transducer element array whose center position corresponds to the center position of the transducer element array composing the transmission aperture Tx for the transmission event. Due to this, the position of the central axis Rxo of the receive aperture Rx for a given transmission event corresponds to the position of the central axis Txo of the transmission aperture Tx for the same transmission event. Further, when transmission events are repetitively performed, the transmission aperture Tx shifts in the transducer element array direction each time, and the receive aperture Rx also shifts in the transducer element array direction in synchronization with the transmission aperture Tx. Thus, a different receive aperture is used to perform delay-and-sum for each transmission event. Accordingly, receive processing with respect to multiple transmission events can be performed by using a group of receive apertures covering a vast measurement area and each differing in terms of time. Thus, uniform spatial resolution is achieved over a vast measurement area.

<<Other Modifications>>

Figure 20B:
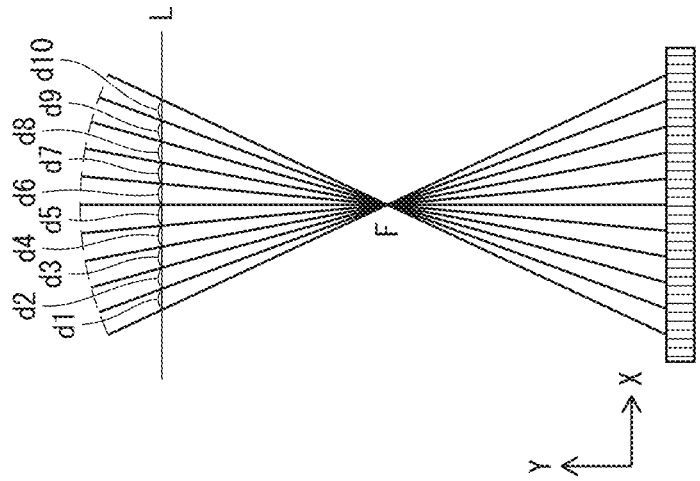
FIGS. 20A and 20B are schematics illustrating other examples of the target line group Bx pertaining to the embodiment.
Figure 20A:
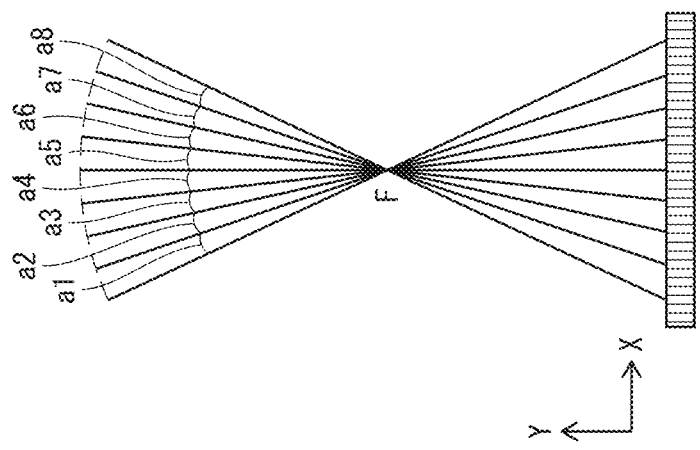

In the embodiment and the modification, an example is described where the target line group Bx is composed of seven target lines equiangularly arranged. However, the present invention is not limited to this, and the target line group Bx suffices as long as it includes at least three target lines, FIG. 20A illustrates an example where the target line group Bx is composed of nine target lines. Further, the positional relationship between target lines is not limited to the relationship where every pair of two adjacent target lines forms a same angle therebetween. For example, the positional relationship between target lines may be such that at the same depth, measurement points on the target lines are spaced away from one another at equal distance. FIG. 20B illustrates an example where the target line group Bx is composed of eleven target lines. In FIG. 20B, the straight line L is parallel to the transducer element array direction, and the distances d1 through d10 between points at which the straight line L intersects the respective target lines are equal.

The target line group Bx is not limited to the examples described above. That is, the target line group Bx may have any shape, provided that the target line group Bx is composed of two or more target lines passing through the transmission focal point F and a distance between two measurement points that are located on two adjacent target lines and that are located at a same distance from the focal point F or are at the same depth is greater than a distance between two adjacent measurement points on one target line. Preferably, the target line group Bx is composed of three or more target lines. In any case, since it is preferable that target lines have different orientations as described above, it is preferable that the target lines be arranged equiangularly or so as to be equally arranged in the transducer element array direction. Further, it is preferable that the maximum of the angle between two target lines be great, and that the target line group Bx includes two target lines matching the outer boundaries of the ultrasound main irradiation area Ax. Further, it is preferable that one of the target lines is located on the transmission aperture central axis Txo. This is since an acoustic line signal with maximum signal intensity can be acquired from such a target line.

(2) Up to this point, the present invention has been described based on a specific embodiment and a modification thereof. However, the embodiment and modification described above are non-limiting examples of application of the present invention, and thus, the present invention shall be construed to encompass the following exemplar modifications.

For example, the present invention may be implemented by using a computer system including a memory storing a computer program and a microprocessor operating based on the computer program. For example, the computer system may store a computer program of the ultrasound signal processing method pertaining to the present invention, and the computer system may operate in accordance with the computer program or may provide instructions in accordance with the computer program to various components connected thereto.

Further, the present invention may be implemented by implementing a part of or the entirety of the ultrasound signal processing device described above, or a part of or an entirety of a beam former described above by using a computer system including a microprocessor, a recording medium such as a ROM or a RAM, and a hard disk unit. In this implementation, a computer program achieving the same operations as a device described above is stored to the RAM or the hard disk unit. Further, in this implementation, various devices achieve their functions by the microprocessor operating in accordance with the computer program.

Further, the present invention may be implemented by implementing some or all components included in a device described above by using one system LSI (large scale integration). A system LSI is an ultra-multifunctional LSI manufactured by integrating multiple components onto one chip. Specifically, a system LSI is a computer system including a microprocessor, a ROM, a RAM, and the like. Further, each component may be separately implemented by using one chip, or some or all components may be implemented by using one chip. Note that LSIs are referred to by using different names, depending upon the level of integration achieved thereby. Such names include IC, system LSI, super LSI, and ultra LSI. In this implementation, a computer program achieving the same operations as any device described above is stored to the RAM. Further, in this implementation, the system LSI achieves its functions by the microprocessor operating in accordance with the computer program. For example, the present invention encompasses a form of implementation where an LSI stores a beam forming method pertaining to the present invention as a program, the LSI is inserted into a computer, and the computer executes the program (i.e., the beam forming method pertaining to the present invention).

Note that integration of circuits may be achieved by a dedicated circuit or a general purpose processor, in addition to being achievable by using an LSI as discussed above. Further, a Field Programmable Gate Array (FPGA), which is programmable after manufacturing, or a reconfigurable processor, which allows reconfiguration of the connection and setting of circuit cells inside the LSI, may be used.

Furthermore, if technology for circuit integration that replaces LSIs emerges, owing to advances in semiconductor technology or to another derivative technology, the integration of functional blocks may naturally be accomplished using such technology.

Further, some or all functions of an ultrasound diagnostic device discussed in the embodiment may be implemented by a processor such as a CPU executing a program. Further, the present invention may be implemented by using a non-transitory computer-readable recording medium having recorded thereon a program causing execution of a diagnostic method and a beam forming method of an ultrasound diagnostic device. Further, execution of the program by another independent computer system may be achieved by transferring the program by recording the program or a signal onto a recording medium. Naturally, the program may be distributed via means of transmission media such as the internet.

The ultrasound diagnostic device pertaining to the embodiment includes the data storage, which is a recording device. However, the recording device need not be included in the ultrasound diagnostic device, and may be implemented by using a semiconductor memory, a hard disk drive, an optical disk drive, a magnetic storage device, or the like connected to the ultrasound diagnostic device from the outside.

Further, the functional blocks illustrated in the block diagrams are mere examples of possible functional blocks. That is, a plurality of functional blocks illustrated in the block diagrams may be combined to form one functional block, a given functional block illustrated in the block diagrams may be divided into a plurality of functional blocks, and a function of a given functional block illustrated in the block diagrams may be transferred to another functional block. Further, with regards to multiple functional blocks having similar functions, such functional blocks may be implemented by one piece of hardware or software executing such functions in parallel or by applying time division.

Further, the above-described order in which steps of processing are executed is a non-limiting example among multiple possible orders that is used for the sole sake of providing specific description of the present invention. Further, some of the steps of processing described above may be executed simultaneously (in parallel).

Further, in the embodiment, description is provided that the ultrasound diagnostic device may have a probe and a display attached thereto. However, the ultrasound diagnostic device may include a probe and a display therein.

Further, in the embodiment, the probe includes a plurality of piezoelectric transducer elements forming a line in one direction. However, the probe may have a different structure. For example, the probe may include a plurality of piezoelectric transducer elements disposed two-dimensionally. Alternatively, the probe may be a swingable probe including a plurality of swingable transducer elements (i.e., transducer elements that can be caused to swing by mechanical means) forming a line in one direction, which enables acquisition of three-dimensional tomographic images. Further, probes of different types may be selected and used depending upon the examination to be performed. For example, when using a probe including piezoelectric transducer elements disposed two-dimensionally, supplying different piezoelectric transducer elements with voltages at different timings or with voltages with different values achieves controlling the position, the direction, etc., of the ultrasound beam to be transmitted.

Further, the probe may be provided with some of the functions of the transmission beam former/receive beam former. For example, the probe may be capable of generating a transmission electric signal based on a control signal that the transmission beam former/receive beam former outputs to cause generation of a transmission electric signal, and of converting the transmission electronic signal into ultrasound. In addition, the probe may be capable of converting reflected ultrasound into a receive electric signal, and of generating a receive signal based on the receive electric signal.

Further, at least some of the functions of the ultrasound diagnostic devices pertaining to the embodiment and the modification may be combined with functions of other ones of the ultrasound diagnostic devices pertaining to the embodiment and the modification. Further, the values used above are non-limiting examples used for the sole sake of providing specific description of the present invention, and may be replaced with other values.

Further, the present invention should be construed as encompassing various modifications that a skilled artisan would arrive at based on the embodiment describe above.

<<Summary>>

(1) One aspect of the present invention is an ultrasound signal processing device that performs multiple transmission events of transmitting converging ultrasound beams to a subject by using an ultrasound probe having multiple transducer elements, that performs, for each of the transmission events, reception of ultrasound reflection from the subject and generation of a sub-frame acoustic line signal based on the ultrasound reflection, and that combines sub-frame acoustic line signals for the respective transmission events to generate a frame acoustic line signal, the ultrasound signal processing device including ultrasound signal processing circuitry configured to operate as: a transmitter that varies a focal point defining a position where ultrasound beams converge between a plurality of transmission events and performs each of the transmission events by causing the ultrasound probe to transmit ultrasound beams directed to an inside of the subject; a receiver that, for each of the transmission events, generates sequences of receive signals for transducer elements of the ultrasound probe based on ultrasound reflection that the ultrasound probe receives from the subject; a delay-and-sum calculator that generates, for each of the transmission events, a sub-frame acoustic line signal including an acoustic line signal for each of a plurality of measurement points located on target lines that pass through the focal point and compose a target line group, the delay-and-sum calculator generating an acoustic line signal for a measurement point by performing delay-and-summing of receive signals, included in the sequences of receive signals, that are based on ultrasound reflection acquired from the measurement point; and a synthesizer that combines sub-frame acoustic line signals for the transmission events to generate a frame acoustic line signal, wherein the target lines are straight lines, and any measurement point, on any of the target lines, that is spaced away from the focal point by a predetermined distance or more satisfies a condition that a distance between the measurement point and a most nearby measurement point on the same target line is smaller than a distance between the measurement point and a most nearby one among measurement points on an adjacent target line.

Another aspect of the present invention is an ultrasound signal processing method in which multiple transmission events of transmitting converging ultrasound beams to a subject are performed by using an ultrasound probe having multiple transducer elements, in which, for each of the transmission events, reception of ultrasound reflection from the subject and generation of a sub-frame acoustic line signal based on the ultrasound reflection are performed, and in which sub-frame acoustic line signals for the respective transmission events are combined to generate a frame acoustic line signal, the ultrasound signal processing method including: varying a focal point defining a position where ultrasound beams converge between a plurality of transmission events and performing each of the transmission events by causing the ultrasound probe to transmit ultrasound beams directed to an inside of the subject; generating, for each of the transmission events, sequences of receive signals for transducer elements of the ultrasound probe based on ultrasound reflection that the ultrasound probe receives from the subject; generating, for each of the transmission events, a sub-frame acoustic line signal including an acoustic line signal for each of a plurality of measurement points located on target lines that pass through the focal point and compose a target line group, an acoustic line signal for a measurement point being generated by performing delay-and-summing of receive signals, included in the sequences of receive signals, that are based on ultrasound reflection acquired from the measurement point; and combining sub-frame acoustic line signals for the transmission events to generate a frame acoustic line signal, wherein the target lines are straight lines, and any measurement point, on any of the target lines, that is spaced away from the focal point by a predetermined distance or more satisfies a condition that a distance between the measurement point and a most nearby measurement point on the same target line is smaller than a distance between the measurement point and a most nearby one among measurement points on an adjacent target line.

The above-described structure and method achieve a reduction in the number of measurement points while suppressing decrease in spatial resolution and S/N ratio of frame acoustic line signals, and thereby achieve a reduction in delay-and-summing computation amount.

(2) In the ultrasound signal processing device of (1), the target line group may include a target line perpendicular to a direction in which the transducer elements of the ultrasound probe are arrayed.

According to the above-described structure, the target line group includes a target line from which an acoustic line signal having maximum signal intensity can be acquired. Thus, the above-described structure achieves an improvement in frame acoustic line signal S/N ratio.

(3) In the ultrasound signal processing device of (1) or (2), the transmitter may select, from among the transducer elements of the ultrasound probe, an array of transmission transducer elements for transmission of the ultrasound beams, and the target line group may include a target line passing through one end of the array of transmission transducer elements and a target line passing through the other end of the array of transmission transducer elements.

According to the above-described structure, the target lines of the target line group are spread out in the direction in which the transducer elements are arranged.

(4) In the ultrasound signal processing device of (3), the target lines of the target line group may all pass through the array of transmission transducer elements.

According to the above-described structure, the target lines of the target line group are spread out as much as possible in the direction in which the transducer elements are arranged within a range where no disturbance in ultrasound beam phase occurs.

(5) In the ultrasound signal processing device of (1) through (4), measurement points located at the same depth may be spaced away from one another at equal distance in a direction in which the transducer elements of the ultrasound probe are arrayed.

The above-described structure achieves uniform measurement point density in the direction in which the transducer elements are arrayed, and thereby enhances the effect of the synthetic aperture method of improving spatial resolution and S/N ratio of frame acoustic line signals.

(6) In the ultrasound signal processing device of (1) through (4), every pair of adjacent target lines of the target line group may form the same angle therebetween.

The above-described structure achieves uniform measurement point density along an arc of a concentric circle centered on the focal point or the focal area, and thereby enhances the effect of the synthetic aperture method of improving spatial resolution and S/N ratio of frame acoustic line signals.

(7) In the ultrasound signal processing device of (1) through (6), the delay-and-sum calculator may use, as a transmission time being a time amount required for transmitted ultrasound to arrive at the measurement point, a total of a first time amount and a second time amount for each measurement point located at a depth no smaller than a focal depth where ultrasound converges inside the subject, and a difference calculated by subtracting the second time amount from the first time amount for each measurement point located at a depth smaller than the focal depth, the first time amount being a time amount required for ultrasound transmitted from a series of transmission transducer elements, among the transducer elements of the ultrasound probe, to arrive at a reference point, the second time amount being a time amount required for transmitted ultrasound to arrive at the measurement point from the reference point.

The above-described structure achieves accurate specification of receive signals in the generation of sub-frame acoustic line signals, and thereby enhances the effect of the synthetic aperture method of improving spatial resolution and S/N ratio of frame acoustic line signals.

(8) In the ultrasound signal processing device of (1) through (7), the target line group may be composed of three or more target lines.

The above-described structure achieves a reduction in computation amount while suppressing decrease in spatial resolution and S/N ratio of frame acoustic line signals.

Although the present invention has been fully described by way of examples with reference to the accompanying drawings, it is to be noted that various changes and modifications will be apparent to those skilled in the art. Therefore, unless such changes and modifications depart from the scope of the present invention, they should be construed as being included therein.

An ultrasound signal processing device pertaining to the present invention, an ultrasound diagnostic device pertaining to the present invention, and an ultrasound signal processing method pertaining to the present invention are useful in improving the performance of conventional ultrasound diagnostic devices, and in particular, are useful in reducing computation device cost and in improving frame rate through reduction in computation load. In addition, the present invention, as well as being applicable to ultrasound, is also applicable for example to sensors having array elements.

What is claimed is:

1. An ultrasound signal processing device that performs multiple transmission events of transmitting converging ultrasound beams to a subject by using an ultrasound probe having multiple transducer elements, that performs, for each of the transmission events, reception of ultrasound reflection from the subject and generation of a sub-frame acoustic line signal based on the ultrasound reflection, and that combines sub-frame acoustic line signals for the respective transmission events to generate a frame acoustic line signal, the ultrasound signal processing device comprising ultrasound signal processing circuitry configured to operate as:

a transmitter that varies a focal point defining a position where ultrasound beams converge between a plurality of transmission events and performs each of the transmission events by causing the ultrasound probe to transmit ultrasound beams directed to an inside of the subject, the focal point being within a main irradiation area of the ultrasound beams;

a receiver that, for each of the transmission events, generates sequences of receive signals for transducer elements of the ultrasound probe based on ultrasound reflection that the ultrasound probe receives from the subject;

a delay-and-sum calculator that generates, for each of the transmission events, a sub-frame acoustic line signal including an acoustic line signal for each of a plurality of measurement points located on target lines that pass through the focal point and compose a target line group, the delay-and-sum calculator generating the acoustic line signal for the each of the plurality of measurement points by performing delay-and-summing of receive signals, included in the sequences of receive signals, that are based on ultrasound reflection acquired from the measurement point; and a synthesizer that combines sub-frame acoustic line signals for the transmission events to generate a frame acoustic line signal, wherein the target lines are straight lines, and each measurement point of the plurality of measurements points that is spaced away from the focal point on one of the plurality of target lines by a predetermined distance or more satisfies a condition that a distance between the each measurement point and a closest neighboring measurement point on a same target line as the each measurement point is smaller than a distance between the each measurement point and any neighboring measurement point on an adjacent target line, which is adjacent to the same target line.

2. The ultrasound signal processing device of claim 1, wherein the target line group includes a target line perpendicular to a direction in which the transducer elements of the ultrasound probe are arrayed.

3. The ultrasound signal processing device of claim 1, wherein the transmitter selects, from among the transducer elements of the ultrasound probe, an array of transmission transducer elements for transmission of the ultrasound beams, and the target line group includes a target line passing through one end of the array of transmission transducer elements and a target line passing through the other end of the array of transmission transducer elements.

4. The ultrasound signal processing device of claim 3, wherein the target lines of the target line group all pass through the array of transmission transducer elements.

5. The ultrasound signal processing device of claim 1, wherein measurement points located at the same depth are spaced away from one another at equal distance in a direction in which the transducer elements of the ultrasound probe are arrayed.

6. The ultrasound signal processing device of claim 1, wherein every pair of adjacent target lines of the target line group form the same angle therebetween.

7. The ultrasound signal processing device of claim 1, wherein the delay-and-sum calculator uses, as a transmission time being a time amount required for transmitted ultrasound to arrive at the each of the measurement points, a total of a first time amount and a second time amount for ones of the measurement points located at a depth no smaller than a focal depth where ultrasound converges inside the subject, and a difference calculated by subtracting the second time amount from the first time amount for ones of the measurement points located at a depth smaller than the focal depth, the first time amount being a time amount required for ultrasound transmitted from a series of transmission transducer elements, among the transducer elements of the ultrasound probe, to arrive at a reference point, the second time amount being a time amount required for transmitted ultrasound to arrive at the each of the measurement points from the reference point.

8. The ultrasound signal processing device of claim 1, wherein the target line group is composed of three or more target lines.

9. An ultrasound diagnostic device comprising:

an ultrasound probe; and an ultrasound signal processing device that performs multiple transmission events of transmitting converging ultrasound beams to a subject by using an ultrasound probe having multiple transducer elements, that performs, for each of the transmission events, reception of ultrasound reflection from the subject and generation of a sub-frame acoustic line signal based on the ultrasound reflection, and that combines sub-frame acoustic line signals for the respective transmission events to generate a frame acoustic line signal, the ultrasound signal processing device comprising ultrasound signal processing circuitry configured to operate as:

a transmitter that varies a focal point defining a position where ultrasound beams converge between a plurality of transmission events and performs each of the transmission events by causing the ultrasound probe to transmit ultrasound beams directed to an inside of the subject, the focal point being within a main irradiation area of the ultrasound beams;

a receiver that, for each of the transmission events, generates sequences of receive signals for transducer elements of the ultrasound probe based on ultrasound reflection that the ultrasound probe receives from the subject;

a delay-and-sum calculator that generates, for each of the transmission events, a sub-frame acoustic line signal including an acoustic line signal for each of a plurality of measurement points located on target lines that pass through the focal point and compose a target line group, the delay-and-sum calculator generating the acoustic line signal for the each of the plurality of measurement points by performing delay-and-summing of receive signals, included in the sequences of receive signals, that are based on ultrasound reflection acquired from the measurement point; and a synthesizer that combines sub-frame acoustic line signals for the transmission events to generate a frame acoustic line signal, wherein the target lines are straight lines, and each measurement point of the plurality of measurements points that is spaced away from the focal point on one of the plurality of target lines by a predetermined distance or more satisfies a condition that a distance between the each measurement point and a closest neighboring measurement point on a same target line as the each measurement point is smaller than a distance between the each measurement point and any neighboring measurement point on an adjacent target line, which is adjacent to the same target line.

10. An ultrasound signal processing method in which multiple transmission events of transmitting converging ultrasound beams to a subject are performed by using an ultrasound probe having multiple transducer elements, in which, for each of the transmission events, reception of ultrasound reflection from the subject and generation of a sub-frame acoustic line signal based on the ultrasound reflection are performed, and in which sub-frame acoustic line signals for the respective transmission events are combined to generate a frame acoustic line signal, the ultrasound signal processing method comprising:

varying a focal point defining a position where ultrasound beams converge between a plurality of transmission events and performing each of the transmission events by causing the ultrasound probe to transmit ultrasound beams directed to an inside of the subject, the focal point being within a main irradiation area of the ultrasound beams;

generating, for each of the transmission events, sequences of receive signals for transducer elements of the ultrasound probe based on ultrasound reflection that the ultrasound probe receives from the subject;

generating, for each of the transmission events, a sub-frame acoustic line signal including an acoustic line signal for each of a plurality of measurement points located on target lines that pass through the focal point and compose a target line group, the acoustic line signal for the each of the plurality of measurement points being generated by performing delay-and-summing of receive signals, included in the sequences of receive signals, that are based on ultrasound reflection acquired from the measurement point; and combining sub-frame acoustic line signals for the transmission events to generate a frame acoustic line signal, wherein the target lines are straight lines, and each measurement point of the plurality of measurements points that is spaced away from the focal point on one of the plurality of target lines by a predetermined distance or more satisfies a condition that a distance between the each measurement point and a closest neighboring measurement point on a same target line as the each measurement point is smaller than a distance between the each measurement point and any neighboring measurement point on an adjacent target line, which is adjacent to the same target line.

11. The ultrasound signal processing device of claim 1, wherein the delay-and-sum calculator sets a signal area in which the measurement points for which acoustic line signals are to be generated for the each of the transmission events.

\* \* \* \* \*